USOO5821234A

United States Patent [19]
Dzau

[11] Patent Number: 5,821,234
[45] Date of Patent: Oct. 13, 1998

[54] INHIBITION OF PROLIFERATION OF VASCULAR SMOOTH MUSCLE CELL

[75] Inventor: Victor J. Dzau, Los Altos, Calif.

[73] Assignee: The Board of Trustees of the Leland Stanford Junior University, Palo Alto, Calif.

[21] Appl. No.: 110,294

[22] Filed: Aug. 20, 1993

Related U.S. Application Data

[63] Continuation-in-part of Ser. No. 63,980, May 19, 1993, abandoned, which is a continuation-in-part of Ser. No. 944,882, Sep. 10, 1992, abandoned.
[51] Int. Cl.$^6$ .............................. A61K 48/00; C12N 5/10
[52] U.S. Cl. .......................... 514/44; 435/375; 435/377; 424/450; 536/24.5; 536/24.3; 536/24.31; 536/24.33
[58] Field of Search .............................. 514/44; 536/24.5, 536/24.3, 24.34, 24.33; 935/34, 9; 435/375, 377; 424/450

[56] References Cited

U.S. PATENT DOCUMENTS

| 4,149,797 | 4/1979 | Imperial ................................ 355/3 FU |
| 5,593,974 | 1/1997 | Rosenberg et al. ........................ 514/44 |

FOREIGN PATENT DOCUMENTS

| 9106309 | 5/1991 | WIPO ............................ A61K 37/22 |
| WO 9301286 | 6/1992 | WIPO ............................ C12N 15/11 |

OTHER PUBLICATIONS

Dzau, V. (1986) Hypertension 8:553–559.
Simons, M., et al. (1992) Nature 359:67–70.
Simons, M. and Rosenberg, R. (1992) Circulation Research 70:835–843.
Speir, E. and Epstein, S. (1992) Circulation 86:538–547.
Rainer, et al. (1991) Hypertension 18:326, abstract 47.
Itoh, et al. (1991) Hypertension 18:325, abstract 46.
Dzau, V. (1988) Circulation 77 (suppl I) 14–113.
Itoh, et al. (1990) J. Clin. Invest. 86:1690–1697.
Campbell–Boswell and Robertson (1981) Exp. and Mol. Pathology 35:265–276.
Naftilan, et al. (1989) Hypertension 13:706–711.
Itoh, et al. (1991) Biochem. Biophys. Res. Comm. 176:1601–1609.
Geisterfer, et al. (1988) Circulation Research 62:749–756.
Gibbons, et al. (1990) Clin. Research 38:287A.
Ferns, et al. (1991) Science 253:1129–1132.
Daemen, et al. (1991) Circulation Research 68:450–456.
Linder, et al. (1991) Circulation Research 68:106–113.
Majesky, et al. (1991) J. Clin. Invest. 88:914–910.
Sarzani, et al. (1989) J. Clin. Invest. 83:1404–1408.
Naftilan, et al. (1989) J. Clin. Invest. 83:1419–1424.
Powell, et al. (1989) Science 245:186–188.
Barret and Benditt (1988) P.N.A.S. 85:2810–2814.
Williams, Richart T. et al. "Identification of a Novel Cyclin-–like Protein in Human Tumor Cells" J. Biol. Chem., vol. 268, No. 12, pp. 8871–8880, Apr. 25, 1993.

Ajchenbaum, Florence, et al. "Independent Regulation of Human D–type Cyclin Gene Expression during $G_1$ Phase in Primary Human T Lymphocytes" J. Biol. Chem., vol. 268, No. 6, pp. 4113–4119, Feb. 25, 1993.
O'Connor, P.M., et al. "$G_2$Delay Induced by Nitrogen Mustard in Human Cells Affects Cyclin A/cdk2 and Cyclin B1/cdc2–Kinase Complexes Differently," J. Biol. Chem., vol. 268, No. 11, pp. 8298–8308, Apr. 15, 1993.
Kato, Keiko, et al. "Expression of Hepatitis B Virus Surface Antigen in Adult Rat Liver" J. Biol. Chem., vol. 266, No. 6, pp. 3361–3364, Feb. 25, 1991.
Rekhter, M. et al. "Cell Proliferation in Human Arteriovenous Fistulas Used For Hemodialysis" Arteriosclerosis and Thrombosis, vol. 13, No. 4 pp. 609–617 Apr., 1993.
B. Tseng et al. Cancer Gene Therapy, vol. 1, No. 1 (Mar. 1994) pp. 65–71.
C. Stein et al. Science, vol. 261, (Aug. 20, 1993) pp. 1004–1012.
P. Westermann et al. Biomed. Biochima. Acta, vol. 48, #1 ('89) pp. 85–93.
A. Thiery et al. in "Gene Regulation: Biology of Antisense RNA & DNA", ed. by R. Erickson et al., NY, Raven Press Ltd. ('92) pp. 147–161.
C. F. Bennett et al. J. Liposome Research, vol. 3, # 1 ('93) pp. 85–102.

(List continued on next page.)

*Primary Examiner*—Charles C. P. Rories
*Attorney, Agent, or Firm*—Pamela J. Sherwood; Bozicevic & Reed LLP

[57] ABSTRACT

This invention encompasses a method for inhibiting vascular cellular activity of cells associated with vascular lesion formation in mammals which involves administering an effective dosage of at least one antisense sequence to at least one gene expressing a cyclin or a cyclin dependent kinase which inhibits the expression of the gene. More particularly, the invention involves administering antisense sequences which inhibit the expression of cyclin A, B1, B2, C, D1, D2, D3, E or cyclin X (p46) cyclin X and cyclin dependent kinase cdc2, cdk2, cdk4 or cdk5. It is preferable to use two antisense sequences each from a different cyclin or cyclin dependent kinase. The cyclin or cyclin kinase depending kinase dosage is preferable administered in combination with proliferating cell nuclear antigen (PCNA). Antisense methods and compositions direct to inhibiting the expression of growth factors such as TGF-$\beta_1$, TGF, bFGF, PDGF are also contemplated by the present invention.

The antisense sequences are incorporated into liposomes, particularly liposomes containing HVJ and which are directly administered intraluminally, intramurally or periadventitiously.

While the method of this invention are useful in treating a broad spectrum of vascular lesions such as lesions in the carotid femural and renal arteries, particularly lesions resulting from renal dialysis fistulas. The invention is particularly useful in treating vascular lesions associated with coronary artery angioplasty.

10 Claims, 3 Drawing Sheets

OTHER PUBLICATIONS

R. Weiss, Science News, vol. 139 (Feb. 16, 1991) pp. 108–109.

M. Barinaga Science, vol. 265 (Aug. 5, 1994) p. 738.

B. Monia et al., J. Biol. Chem., vol. 267 (Oct. 5, 1992) pp. 19954–19962.

E. Wickstrom et al. The FASEB Journal, vol. 5 #5 (Mar. 15, 1991) p. A1443.

M. Ebbecke et al. Eur. Heart J., vol. 12, Abstr. Suppl., ('91) p. 11.

Y. Furukawa et al. Science, vol. 250 (Nov. 9, 1990) pp. 805–808.

D. Jaskulski et al Science, vol. 240 (Jun. 10, 1988) pp. 1544–1546.

P. Felques et al. PNAS, vol. 84 (Nov. '87) pp. 7413–7417.

R. Mannino et al. Bio/Techniques, vol. 6, #7 ('88) pp. 682–690.

J. Wang et al. Nature, vol. 343, (Feb. 8, 1990) pp. 555–557.

L. H. Tsai et al. Nature, vol. 353 (Sep. 12, 1991) pp. 174–177.

J. Pines Cell, vol. 58 (Sep. 8, 1989) pp. 833–846.

Y. Kaneda et al. Expt'l. Cell Res., vol. 173 ('87) pp. 56–69.

J. Holt et al. Mol. Cell. Biol., vol. 8 #2 (Feb. '88) pp. 963–973.

Life Technologies /GIBCO–BRL catalog, 1993–1994, Gaithersburg MD, pp. 9–19.

P. Hug et al., Biochem Biophys. Acta, vol. 1097 ('91) pp. 1–17.

A. Clowes et al. J. Cardiovasc. Pharmacology, vol. 14, Sep. 6 ('89) pp. 512–515.

P. Libby et al. Circulation, vol. 86, #6, Suppl.III (Dec. 1992) pp. III47–III52.

R. Mosley et al (abstract) Am. J. Gastroenterol., vol. 89, #10 (Oct. 1994) pp. 1874–1879.

D. Liu et al. (abstract) Clin. Exp. Hypertens., vol. 16 #4 (Jul. 1994) pp. 391–414.

E. Uhlmann et al. Chemical Reviews, vol. 90, #4 (Jun. '90) pp. 543–584.

E. Wickstrom et al., FASEB J. 5(5) (Mar. 15, 1991) A1443.

M. Ebbeske et al., Eur Heart J. 12 (Abstr. Suppl.) ('91) 11.

Y. Furukawa et al., Science 250 (Nov. 9, 1990) 805–808.

A. Clowes et al. J. Cardiovasc. Pharm. 14(Suppl. 6) (89) 512–515.

Y. Kaneda et al., Expt. Cell Res. 173 ('87) 56–69.

A. Lafont et al. Lancet 346 (Dec. 2, 1995) 1442–1443.

J. Milligan et al., J. Med. Chem. 36 (14) (Jul. 9, 1993) 1923–37.

M. Barinaga, Science 265 (Aug. 5, 1994) 738.

R. Weiss, Science News 139 (Feb. 16, 1991) 108–9.

C. Stein et al,. Science 261 (Aug. 20, 1993) 1004–12.

E. Uhlmann et al,. Chem. Res. 90 (4) (Jun. 1990) 543–84.

B. Tseng et al., Cancer Gene Ther. 1 (1) (Mar. 1994) 65–71.

P. Westermann et al. Biomed. Biochim. Acta 48(1) ('89) 85–93.

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:1:

GCCUCCCCCA UGCCGCCCUC CGGG     24

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGAGGGCGGC ATGGG     15

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCCATGCCGC CCTCC     15

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGGTACGGCG GGAGG     15

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear (  i  i  ) MOLECULE TYPE: mRNA (  x  i  ) SEQUENCE DESCRIPTION: SEQ ID NO:5:

GCAGCAGGGA  CCAUGGCAGC  CGGGAGC                                                                 2 7

( 2 ) INFORMATION FOR SEQ ID NO:6:

(  i  ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i  i  ) MOLECULE TYPE: cDNA (  x  i  ) SEQUENCE DESCRIPTION: SEQ ID NO:6:

GGCTGCCATG  GTCCC                                                                                1 5

( 2 ) INFORMATION FOR SEQ ID NO:7:

(  i  ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i  i  ) MOLECULE TYPE: cDNA (  x  i  ) SEQUENCE DESCRIPTION: SEQ ID NO:7:

GGGACCATGG  CAGCC                                                                                1 5

( 2 ) INFORMATION FOR SEQ ID NO:8:

(  i  ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i  i  ) MOLECULE TYPE: cDNA (  x  i  ) SEQUENCE DESCRIPTION: SEQ ID NO:8:

CCCTGGTACC  GTCGG                                                                                1 5

( 2 ) INFORMATION FOR SEQ ID NO:9:

(  i  ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear (  i  i  ) MOLECULE TYPE: mRNA (  x  i  ) SEQUENCE DESCRIPTION: SEQ ID NO:9:

CGGGACGCGA  UGAGGACCUU  GGCU                                                                     2 4

( 2 ) INFORMATION FOR SEQ ID NO:10:

(  i  ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i  i  ) MOLECULE TYPE: cDNA (  x  i  ) SEQUENCE DESCRIPTION: SEQ ID NO:10:

AGCCAAGGTC CTCAT  15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ATGAGGACCT TGGCT  15

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:12:

UGAGUAACUA UGGAAGACUA UAUC  24

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GTCTTCCATA GTTACTCA  18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TGAGTAACTA TGGAAGAC  18

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:15:

AACUCCGCCA CCAUGUUUGA GGCAGGCCUG  30

( 2 ) INFORMATION FOR SEQ ID NO:16:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

CTCAAACATG GTGGC     15

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GATCAGGCGT GCCTCAAA     18

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

GCCACCATGT TTGAG     15

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TTTGAGGCAC GCCTGATC     18

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:20:

GGAGCCAUGG CGCUCAGGGU C     21

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

CCTGAGCGCC ATGGCTCC    18

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

GGAGCCATGG CGCTCAGG    18

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:23:

UGGCGCUUCA UGGAGAACUU CCAA    24

( 2 ) INFORMATION FOR SEQ ID NO:24:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GAAGTTCTCC ATGAAGCG    18

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CGCTTCATGG AGAACTTC    18

( 2 ) INFORMATION FOR SEQ ID NO:26:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
TTGACTAACT ATGGAAGATT ATACCAAAAT AGAGAAAATT GGAGAAGGTA CCTATGGAGT         60

TGTGTATAAG GGT                                                            73
```

( 2 ) INFORMATION FOR SEQ ID NO:27:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

```
GGGAGCAGTG ATGTTGGGGC AACTCTGCGC CGGGGCCTGC G                             41
```

( 2 ) INFORMATION FOR SEQ ID NO:28:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

```
AGAGGAAGCC ATGGCGCTCC GAGTCACCAG GAACTCGAAA ATTAATGCTG AAAATAAGGC         60

GAAGATCAAC ATG                                                            73
```

( 2 ) INFORMATION FOR SEQ ID NO:29:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
GGCTGGGTCT ATGGTCGCTC CGCGGCCGTC CGCCGCGTGG TGCTTTTTTA TCAGGGAAAG         60

CTGTGTTCCA TGGCAGGGAA C                                                   81
```

( 2 ) INFORMATION FOR SEQ ID NO:30:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
AGCCCCAGCC ATGGAACACC AGCTCCTGTG CTGCGAAGTG GAAACCATCC GCCGCGCGCT         60

ACCCCGATGC CAACCTCCTC AAC                                                 83
```

( 2 ) INFORMATION FOR SEQ ID NO:31:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

CTGCCCGAGT ATGGAGCTGC TGTGTTGCGA AGGCACCCGG CACGCGCCCC GGGCCGGGCC    60

GGACCCGCGG CTGCTGGG    78

( 2 ) INFORMATION FOR SEQ ID NO:32:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

GCGGGACACC ATGAAGGAGG ACGGCGGCGC GGAGTTCTCG GCTCGCTCCA GGAAGAGGAA    60

GGCAAACGTG ACCGTTTTTT G    81

( 2 ) INFORMATION FOR SEQ ID NO:33:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

CTCCGCCACC ATGTTCGAGG CGCGCCTGGT CCAGGGCTCC ATCCTCAAGA AGGTGTTGGA    60

GGCACTCAAG GACCTC    76

( 2 ) INFORMATION FOR SEQ ID NO:34:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

TGAGTAACTA TGGAAGAC    18

( 2 ) INFORMATION FOR SEQ ID NO:35:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

GTCTTCCATA GTTACTCA    18

( 2 ) INFORMATION FOR SEQ ID NO:36:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

TGAGTAACTA TGGAGGAC  18

( 2 ) INFORMATION FOR SEQ ID NO:37:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

GTCTTCCATA GTTACTCA  18

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

TTTGAGGCAC GCCTGATC  18

( 2 ) INFORMATION FOR SEQ ID NO:39:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

GATCAGGCGT GCCTCAAA  18

( 2 ) INFORMATION FOR SEQ ID NO:40:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

CGCTTCATGG CGAACTTC  18

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

GAAGTTCTCC ATGAAGCG  18

( 2 ) INFORMATION FOR SEQ ID NO:42:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:42:

GAAGGAGCCA TGGCGCTC 18

( 2 ) INFORMATION FOR SEQ ID NO:43:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:43:

GAGCGCCATG GCTCCTCC 18

( 2 ) INFORMATION FOR SEQ ID NO:44:

( i ) SEQUENCE CHARACTERISTICS:
       ( A ) LENGTH: 19 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:44:

CTTCGTCGGT ACCGTCTTC 19

( 2 ) INFORMATION FOR SEQ ID NO:45:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:45:

ACCCAGAAAG AAAATCCC 18

( 2 ) INFORMATION FOR SEQ ID NO:46:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:46:

CGCTTCATGG AGAACTTC 18

( 2 ) INFORMATION FOR SEQ ID NO:47:

( i ) SEQUENCE CHARACTERISTICS:

```
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:47:

ATGGCAGAAA GCTAGGCC                                                                       1 8

( 2 ) INFORMATION FOR SEQ ID NO:48:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:48:

TTGTAACCAA CTGGGACGAT ATGG                                                                2 4

( 2 ) INFORMATION FOR SEQ ID NO:49:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:49:

GATCTTGATC TTCATGGTGC TAGG                                                                2 4
```

INHIBITION OF PROLIFERATION OF VASCULAR SMOOTH MUSCLE CELL

REFERENCE TO RELATED APPLICATIONS

This is a continuation-in-part of U.S. Ser. No. 08/063,980 filed May 19, 1993, now abandoned, which in turn is a continuation-in-part of U.S. Ser. No. 07/944,882 filed Sep. 10, 1992, now abandoned, the contents of both which are incorporated herein by reference.

The work disclosed herein was supported by NIH grants HL35610, HL35252, HL42663 and the University of California Tobacco-Related Disease Program IRT215. The United States Government may have rights in the invention.

BACKGROUND OF THE INVENTION

1. Technical Field

The field of this invention is inhibition of cellular activity related to vascular lesions.

2. Background of The Related Art

In the growth and maintenance of multi-cellular organisms, the organism has had to develop processes to activate or inhibit the proliferation of cells. The organism has developed numerous mechanisms, whereby signals are given to cells, by either intracellular or extracellular messengers. Control of proliferation provides for modeling of organs, maintenance of subsets of leukocytes in hematopoiesis, wound healing and the like. However, in many situations, such as injury or disease states, the response of the organism to the injury or disease may, in fact, be deleterious to the health of the organism.

The vascular response to injury involves an alteration in three fundamental cellular processes; cell growth, cell migration and extracellular matrix production. This vascular response to injury is characteristic of the pathogenesis of various vascular diseases including (but not limited to): atherosclerosis, restenosis after angioplasty, vein bypass graft stenosis, prosthetic graft stenosis, angiogenesis and hypertension. For example, atherosclerotic lesions evolve as a result of vascular smooth muscle migration into the subintimal space, proliferation and the production of abundant extracellular matrix. Similarly, restenosis after angioplasty, vein bypass graft stenosis, prosthetic graft stenosis, angiogenesis and hypertension involve abnormalities in vascular cell growth, migration and matrix composition. The precise mechanisms responsible for alterations in the regulation of these cellular processes are poorly characterized.

Dzau, *Hypertension* 8, 553–559 (1986) describes the vascular renin-angiotensin pathway. Geisterfer, et al., *Circulation Research* 62, 749–756 (1988) report that angiotensin II induces hypertrophy of cultured rat aortic smooth muscle cells. Barrett and Benditt, *Proc. Natl. Acad. Sci. USA* 85, 2810–2814 (1988) describe the expression of platelet-derived growth factor in human atherosclerotic plaques and normal artery wall. Powell, et al., *Science* 245, 186–188 (1989) report that inhibitors of angiotensin-converting enzyme prevent myointimal proliferation after vascular injury. Naftilan, et al.,*J. Clin. Invest.* 83, 1413–1424 (1989) report the induction of platelet-derived growth factor A chain and c-myc gene expression by angiotensin II in cultured rat vascular smooth muscle cells. Sarzani, et al., *J. Clin. Invest.* 83, 1404–1408 (1989) describe the expression of various growth factors in aorta or normotensive and hypertensive rats. Majesky, et al., *J. Clin. Invest.*, 88, 904–910 (1991) report the production of TGF-$\beta_1$ during repair of arterial injury. Linder, et al., *Circulation Research,* 68, 106–113 (1991) describe the role of basic fibroblast growth factor in vascular lesion formation. Daemen, et al., *Circulation Research,* 68, 450–456 (1991) report the role of angiotensin II in inducing smooth muscle cell proliferation in the normal and injured rat arterial wall. Ferns, et al., *Science,* 253, 1129–1132 (1991) report the inhibition of neointimal smooth muscle accumulation after angioplasty by an antibody to PDGF, Gibbons, et al., *Clin. Research,* 38, 287A (1990) report the modulation by transforming growth factor-$\beta$ of the bifunctional growth response of vascular smooth muscle cells to angiotensin II. Itoh, et al., *Biochem. Biophys. Res. Comm.,* 176, 1601–1609 (1991) report the interaction of atrial natriuretic polypeptide and angiotensin II on protooncogene expression and vascular cell growth.

Simons and Rosenberg, *Circ. Res.,* 70, 835–843 (1992) report that antisense oligonucleotides to non-muscle myosin heavy chain and c-myb suppress smooth muscle cell proliferation in vitro. Speir and Epstein, *Circulation,* 86, 538–547 (1992) report that antisense to proliferating cell nuclear antigen (PCNA) inhibits smooth muscle cell proliferation in vitro. Rosenberg et al., PCT/US92/05305, January 1993 describes an antisense approach of localized oligonucleotide therapy involving the inhibition of the c-myb or PCNA protein.

The relationship of the expression of cyclins at various phases of the cell synthesis and mitosis cycle are described in *The Journal of NIH Research*, December 1992, Vol. 4, pp. 55–59. FIG. 1 for example shows the approximate level of Cyclins A, B1, B2, C, D1, D2 and E during G1 (gap 1), synthesis, G2 (gap 2) and mitotic phase of cell proliferation. Williams, et al., *The Journal of Biological Chemistry*, Vol. 266, No. 12, Apr. 25 (1993), pp. 8871–8880 shows the isolation of cyclin x (p46).

Both of these later two articles and references such as O'Connor, et al., *The Journal of Biological Chemistry*, Vol. 286, No. 11, April 15, pp. 8298–8308 (1993) elucidate the interaction of various Cyclin dependent kinases such as cdc2 and cdk2 and Cyclins A and B.

Jaskulski et al., *Science*, Vol. 240, No. 4858, pp. 1544–6 (1988) describes the effects of antisense oligonucleotides on growing Balb/C313 cells. It was shown that the antisense molecule inhibited synthesis and mitosis and sense oligos had no effect. Sala et al., *Proc. Natl. Acad. Sci., USA*, Vol. 89, No. 21, pp. 10415–9 (Nov. 1992) describes antisense sequences to c-myb gene which inhibit c-myb expression. Kimeki, *J. Cell Biochem*, Vol. 50, No. 1, pp. 1–9 (1992) describes antisense interruption of C-myc or Cyclin A in vitro. Doyle et al., *Antisense Res. Dev.*, Vol. 1, No. 1 Spring, pp. 11–20 (1991) describes antisense oligonucleotides to Cyclin B in xenopus oocytes. Zindly et al., *Biochem Biophys. Res. Commun.*, Vol. 1897, No. 3, pp. 1144–54 (1992) describes antisense interruption of the production of Cyclin A or Cyclin B in rats. Cyclin A antisense oligonucleotides are also described in *Nature*, Vol. 354, No. 6351, pp. 314–7 (1991) and Guerria et al., *EMBO J.*, Vol. 10, No. 11, pp. 3343–9 (1991). These references report the effect of Cyclin A or Cyclin B oligos in metaphase I oocytes. Further, antisense studies in xenopus embryos are described in *Development*, Vol. III, No. 4 pp. 1173–8 (1991) and *J. Cell. Biol.*, Vol. 114, No. 4, pp. 767–72 (1991). Lapidot-Lifson et al., *Proc. Natl. Acad. Sci., USA*, Vol. 89, No. 2, pp. 579–83 (1992) describe the down regulation of cdc2 with antisense oligonucleotides.

SUMMARY OF THE INVENTION

This invention encompasses a method for inhibiting vascular cellular activity of cells associated with vascular lesion formation in mammals which involves administering an effective dosage of at least one antisense sequence to at least one mRNA or pre-LRNA for a gene for a cyclin or a cyclin dependent kinase which antisense sequence inhibits the expression of the gene. More particularly, the invention involves administering antisense sequences which inhibit the expression of cyclin A, B1, B2, C, D1, D2, D3, E or cyclin X (p46) and cyclin dependent kinase cdc2, cdk2, cdk4 or cdk5. It is preferable to use two antisense sequences each which inhibits expression of a different cyclin or cyclin dependent kinase.

In another aspect, the antisense sequence against cyclin or cyclin dependent kinase is preferably administered in combination with an antisense sequence against proliferating cell nuclear antigen (PCNA).

Antisense methods and compositions directed to inhibiting the expression of growth factors such as transforming growth factor beta (TGFβ), basic fibroblast growth factor (bFGF) and platelet derived growth factor (PDGF) are also contemplated by the present invention.

The antisense sequences are incorporated into liposomes, particularly liposomes containing HVJ and which are directly administered intraluminally, intramurally or periadventitiously.

While the methods of this invention are useful in treating a broad spectrum of vascular lesions. Such lesions include, but are not limited to, lesions in the carotid femoral and renal arteries, particularly lesions resulting from renal dialysis fistulas. The methods of the present invention are particularly useful in treating vascular lesions associated with cardiovascular angioplasty. For such use, the antisense sequence is applied to the angioplasty site to reduce restenosis.

DETAILED DESCRIPTION OF THE INVENTION

Figure 1:
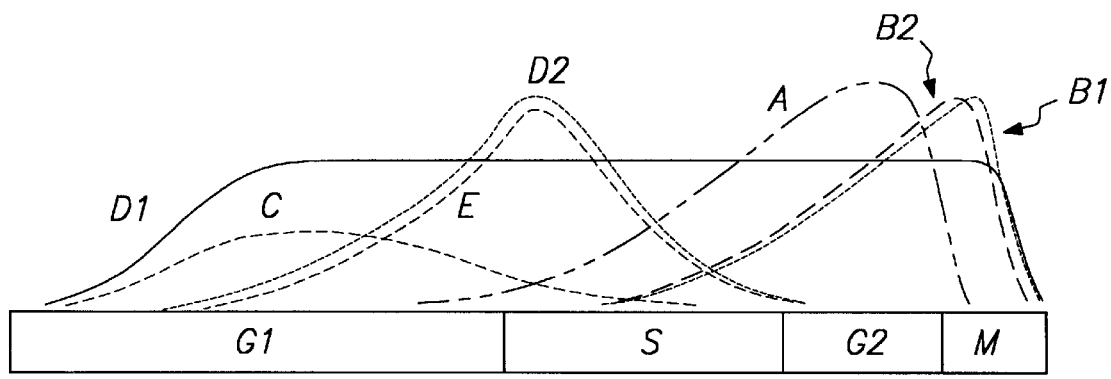
Figure 2:
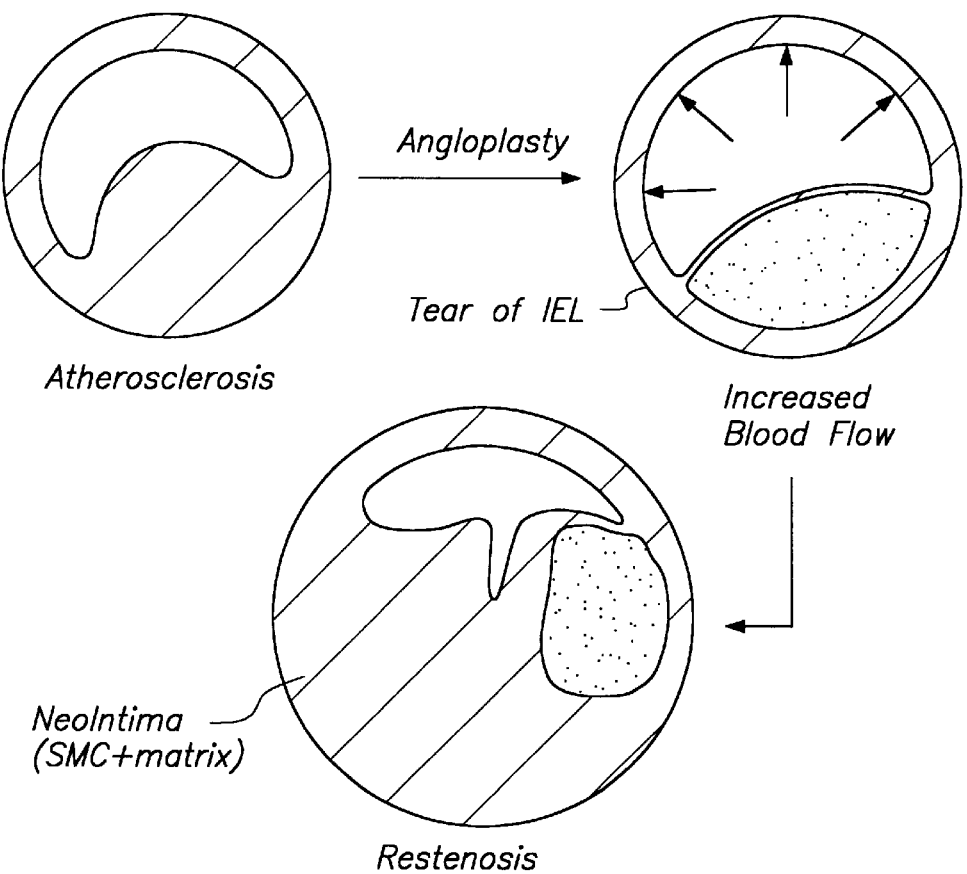
Figure 3:
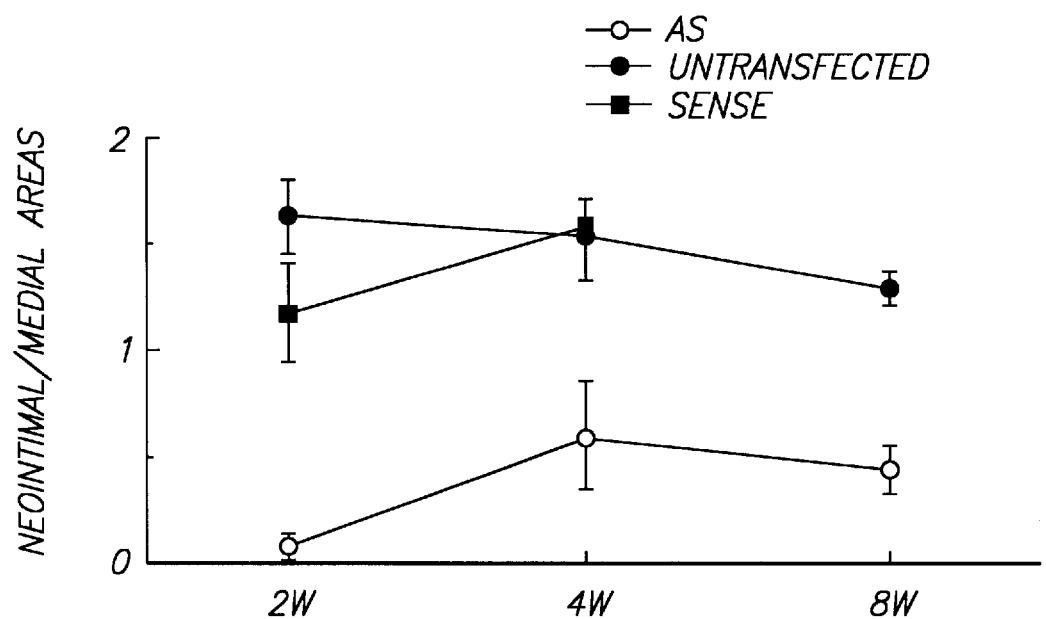
Figure 4:
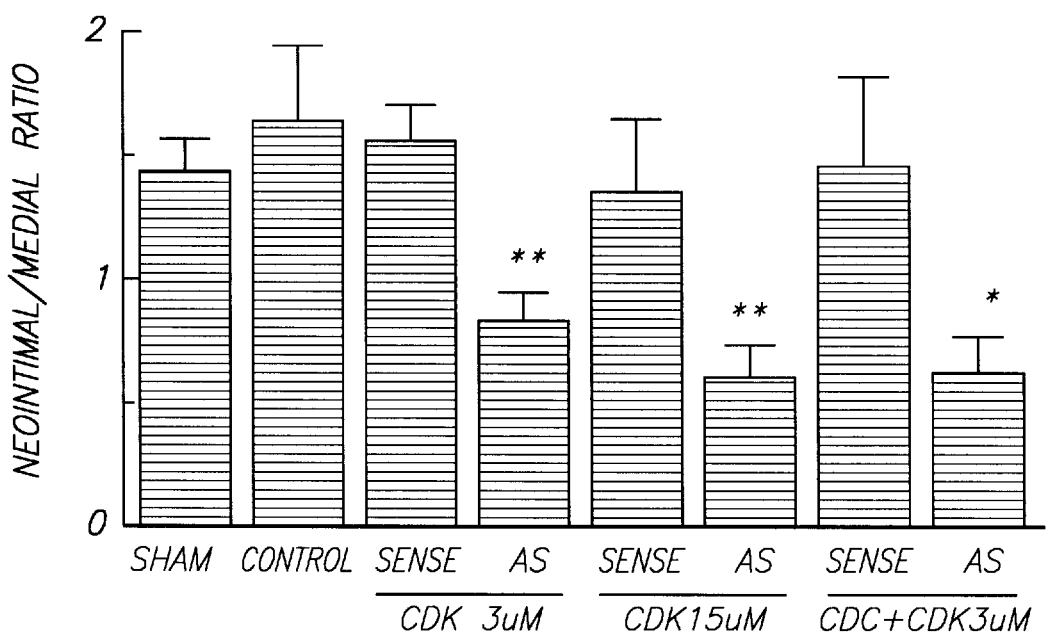

Brief Description of the Drawings FIG. 1 is a schematic diagram of the appropriate level of various cyclins in G1, S, G2, or M phase states of the cell cycle FIG. 2 shows the histology of restenosis FIG. 3 shows the effect of combined antisense treatment against cdc2 and PCNA on neointima with time FIG. 4 shows the effect of antisense against cdk2 and cdc2 on neointimal/media areas ratio.

Figure 5:
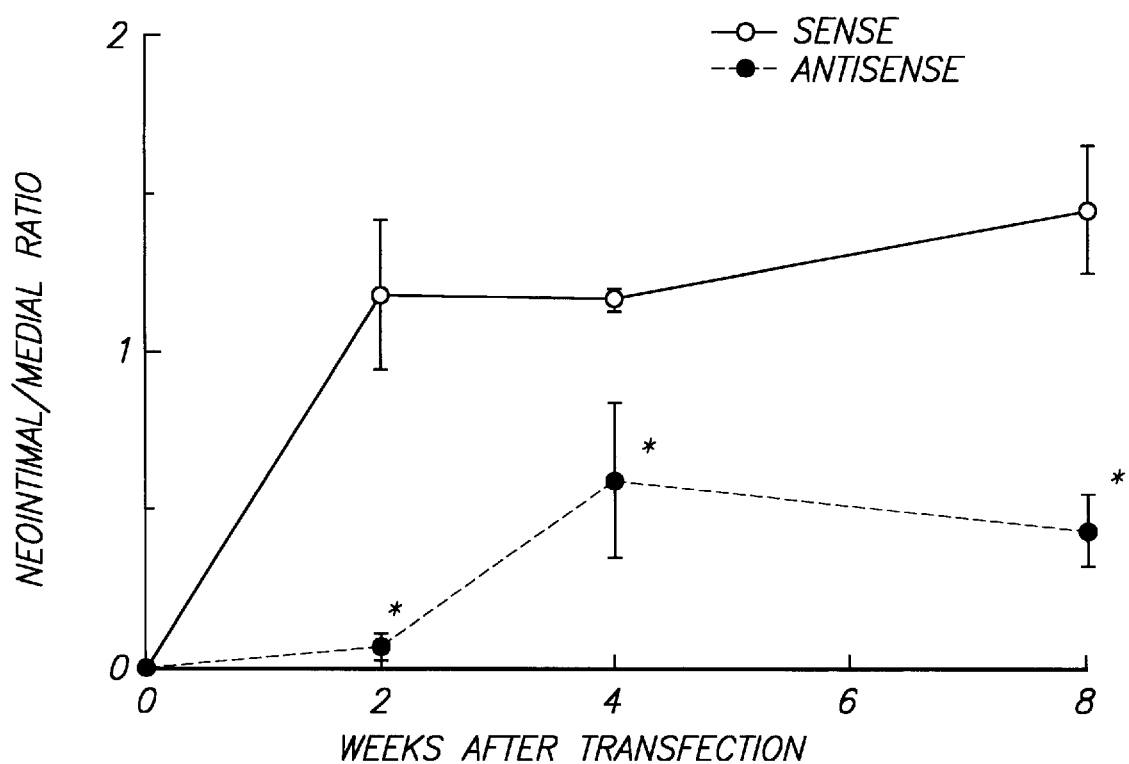

FIG. 5 long term efficiency of antisense and sense ODN of cdc2 kinase/PCN on intimal/medial area ratio. **P<0.01 vs. sense.

The approximate levels of expression of cyclins during the cell cycle are shown in FIG. 1, Cyclin D, appears in the gap 1 (G1) phase and is expressed throughout the cycle in the presence of growth factors. Cyclin C accumulates in early G1 and then declines. Cyclin D2 and E accumulate at the end of G1 and are degraded during synthesis (S) phase Cyclin A is first detected in the (S) phase and is degraded as the cells enter mitosis (M). Cyclins B1 and B2 appear soon after cyclin A and are degraded in mid-M phase. These cyclins are important proteins in the cell cycle and are recognized as a family of related proteins by their amino acid sequence homology. Cyclins form active complexes with kinases and these active complexes phosphorylate proteins.

FIG. 2 illustrates the restenosis process after angioplasty. Angioplasty is performed by inflating a balloon in an artery to relieve an obstructive atherosclerotic lesion. In the course of compressing the lesion the procedure induces tearing of the internal elastic laminae (IEL). Increased blood flow results from relief of the narrowing. The tears in the IEL and injury of the blood vessel wall by the balloon expansion induce a vascular smooth muscle cell proliferative response that results in formation of a neointima and renewed obstruction to the vessel lumen. The neointima consists of smooth muscle cells and matrix and takes 1–6 months to form post angioplasty.

Tables 1 and 2 illustrate sense and antisense sequences for various growth factors, for representative cyclins or, cyclin dependent kineses, and PCNA. Table 3 illustrates various human DNA sequences useful for deriving antisense sequence information for making therapeutic agents of this invention. Table 4 illustrates the sequence of ODN against cell regulatory genes used in various examples. Table 5 are antisense ODN on neointima/medial area ratios as determined in Example 4.

TABLE 1

| | Genbank Accession # |
|---|---|
| A. human TGF-$\beta_1$ MRNA: Nature 316, 701–706 (1985), | X02812 |
| 5'-GCC UCC CCC AUG CCG CCC UCC GGG-3' (SEQ ID NO: 1) | J05114 |
| antisense TGF: | |
| 3'-GGG TAC GGC GGG AGG-5' (SEQ ID NO: 2) | |
| control TGF: | |
| sense TGF: | |
| 5'-CCC ATG CCG CCC TCC-3 (SEQ ID NO: 3) | |
| reverse TGF: | |
| 5'-GGG TAC GGC GGG AGG-3' (SEQ ID NO: 4) | |
| B. human BFGF MRNA: N.Y. Acad. Sci. 638, 109–123 (1991) | |
| Biochem, Biophys. Res. Commun. 144 543–550 (1988) | |
| (GCA) 5'-GCA GGG ACC AUG GCA GCC GGG AGC-3' (SEQ ID NO: 5) | M17599 |
| | S81809 |
| antisense FGF: | |
| 3'-CCC TGG TAC CGT CGG-5' (SEQ ID NO: 6) | |
| control FGF: | |

TABLE 1-continued

| | Genbank Accession # |
|---|---|
| sense FGF: | |
| 5'-GGG ACC ATG GCA GCC-3' (SEQ ID NO: 7) reverse FGF: | |
| 5'-CCC TGG TAC CGT CGG-3' (SEQ ID NO: 8) | |
| C. human PDGF A chain mRNA: Nature 320, 695–699 (1986) 5'-CGG GAC GCG AUG AGG ACC UUG GCU-3' (SEQ ID NO: 9) antisense PDGF: | X03795 |
| 3'-TAC TCC TGG AAC CGA-5' (SEQ ID NO: 10) control PDGF: sense PDGF: | |
| 5'-ATG AGG ACC TTG GCT-3' (SEQ ID NO: 11) | |

TABLE 2

| | Genbank Accession # |
|---|---|
| A. Mouse cdc2 mRNA | |
| 5'-UGA GUA ACU AUG GAA GAC UAU AUC-3' (SEQ ID NO: 12) Antisense | X16461 |
| 3'-ACT CAT TGA TAC CTT CTG-5' (SEQ ID NO: 13) Sense | |
| 5'-TGA GTA ACT ATG GAA GAC-3' (SEQ ID NO: 14) | |
| B. Rat PCNA mRNA 5'-AAC UCC GCC ACC AUG UUU GAG GCA GGC CUG-3' (SEQ ID NO: 15) Antisense | Y00047 and M24604 |
| 1: −6 +9 3'-CGG TGG TAC AAA CTC-5' (SEQ ID NO: 16) 2: +4−+21 3'-AAA CTC CGT GCG GAC TAG-5' (SEQ ID NO: 17) Sense | |
| 1: −6 +9 5'-GCC ACC ATG TTT GAG-3' (SEQ ID NO: 18) 2: +4−+21 5'-TTT GAG GCA CGC CTG ATC-3' (SEQ ID NO: 19) | |
| C. Rat cyclin B mRNA 5'-GGA GCC AUG GCG CUC AGG GUC-3' (SEQ ID NO: 20) Antisense Cyclin B | X60768 |
| 3'-CCT CGG TAC CGC GAG TCC-5' (SEQ ID NO: 21) Sense Cyclin B | |
| 5'-GGA GCC ATG GCG CTC AGG-3' (SEQ ID NO: 22) | |

TABLE 3

| | Genbank Accession # |
|---|---|
| A. Human cdk2 mRNA, EMBO J 10 2653–2659 (1990) 5'-UGG CGC UUC AUG GAG AAC UUC CAA-3' (SEQ ID NO: 23) Antisense cdk2: | X61622 |
| 3'-GCG AAG TAC CTC TTG AAG-5' (SEQ ID NO: 24) Control | |
| Sense cdk2 5'-CGC TTC ATG GAG AAC TTC-3' (SEQ ID NO: 25) | |

TABLE 3-continued

| | Genbank Accession # |
|---|---|
| B. Human cdc2, Nature 327:31–35 (1987)<br>5'-TTGACTAACTATGGAAGATTATACCAAAATAGAGAAAATT<br>GGAGAAGGTACCTATGGAGTTGTGTATAAGGGT-3' (SEQ ID NO: 26) | X05360 |
| C. Human cyclin A Nature 343:555–557 (1990)<br>5'-GGGAGCAGTGATGTTGGGGCAACTCTGCGCCGGGGCCTGCG (SEQ ID NO: 27) | X51688 |
| D. Human cyclin B Cell 58:833–846 (1989)<br>5'-AGAGGAAGCCATGGCGCTCCGAGTCACCAGGAACTCGAAA<br>ATTAATGCTGAAAATAAGGCGAAGATCAACATG-3' (SEQ ID NO: 28) | M25753 |
| E. Human cyclin C Cell 66:1197–1206 (1991)<br>5'-GGCTGGGTCTATGGTCGCTCCGCGGCCGTCCGCCGCGTGG<br>TGCTTTTTATCAGGGCAAGCTGTGTTCCATGGCAGGGAAC-3' (SEQ ID NO: 29) | M74091 |
| F. Human cyclin D1 Cell 66:1197–1206 (1991)<br>5'-AGCCCCAGCCATGGAACACCAGCTCCTGTGCTGCGAAGTGG<br>AAACCATCCGCCGCGCGCTACCCCGATGCCAACCTCCTCAAC-3' (SEQ ID NO: 30) | M74092 |
| G. Human cyclin D3 J. Biol. Chem. 267:20412–20415 (1992)<br>5'-CTGCCCGAGTATGGAGCTGCTGTGTTGCGAAGGCACCCGGC<br>ACGCGCCCGGGCCGGGCCGGACCCGCGGCTGCTGGG-3' (SEQ ID NO: 31) | M92287 |
| H. Human cyclin E Cell 66:1197–1206 (1991)<br>5'-GCGGGACACCATGAAGGAGGACGGCGGCGCGGAGTTCTCGG<br>CTCGCTCCAGGAAGAGGAAGGCAAACGTGACCGTTTTTTG-3' (SEQ ID NO: 32) | M74093 |
| I. Human PCNA J. Biol. Chem. 264:7466–72 (1989)<br>5'-CTCCGCCACCATGTTCGAGGCGCGCCTGGTCCAGGGCTCCA<br>TCCTCAAGAAGGTGTTGGAGGCACTCAAGGACCTC-3' (SEQ ID NO: 33) | J04718 |

TABLE 4

Sequences of Antisense ODN.

1) cdc2 (position −9 to +9 of the mouse sequence)

Sense 5'-TGA—GTA—ACT—ATG—GAA—GAC-3' (SEQ ID NO: 34)
 Antisense 5'-GTC—TTC—CAT—AGT—TAC—TCA-3' (SEQ ID NO: 35)

2) cdc2 (position −9 to +9 of the rat sequence)

Sense 5'-TGA—GTA—ACT—ATG—GAG—GAC-3' (SEQ ID NO: 36)
 Antisense 5'-GTC—TTC—CAT—AGT—TAC—TCA-3' (SEQ ID NO: 37)

3) PCNA (position +4 to +22 of the rat sequence)

Sense 5'-TTT—GAG—GCA—CGC—CTG—ATC-3' (SEQ ID NO: 38)
 Antisense 5'-GAT—CAG—GCG—TGC—CTC—AAA-3' (SEQ ID NO: 39)

4) cdk 2 (position −6 to +12 of human sequence)

Sense 5'-CGC—TTC—ATG—GCG—AAC—TTC-3' (SEQ ID NO: 40)
 Antisense 5'-GAA—GTT—CTC—CAT—GAA—GCG-3' (SEQ ID NO: 41)

5) cyclin B1 (position −9 to +9 of rat sequence)

Sense 5'-GAA—GGA—GCC—ATG—GCG—CTC-3' (SEQ ID NO: 42)
 Antisense 5'-GAG—CGC—CAT—GGC—TCC—TCC-3' (SEQ ID NO: 43)

6) Scrambled ODN

5'-CTT—CGT—CGG—TAC—CGT—CTT—C-3' (SEQ ID NO: 44)

7) thrombomodulin

Antisense 5'-ACC—CAG—AAA—GAA—AAT—CCC-3' (SEQ ID NO: 45)

TABLE 5

Effect of antisense ODN on neointima/medial areas ratio

| | SENSE | ANTISENSE | UNTRANSFECTED |
|---|---|---|---|
| PCNA | n.t. | 1.460 ± 0.193 | n.t. |
| cdc2 kinase | | | |
| mouse | 1.250 ± 0.188 | 0.741 ± 0.126* | 1.244 ± 0.253 |
| rat | n.t. | 0.814 ± 0.201** | 1.856 ± 0.208 |
| cdk 2 | 1.341 ± 0.307 | 0.597 ± 0.131** | 1.156 ± 0.077 |
| cdc 2 (mouse) + PCNA | 1.174 ± 0.235 | 0.084 ± 0.06** | 1.510 ± 0.203 |
| cdc 2 (rat) + PCNA | n.t. | 0.130 ± 0.074** | 0.931 ± 0.27 |
| cdc 2 (rat) + cyclin B1 | n.t. | 0.267 ± 0.029** | 1.220 ± 0.189 |
| cdc 2 (mouse) + cdk 2 | 1.440 ± 0.366 | 0.283 ± 0.188** | n.t. |
| scrambled | 1.695 ± 0.136 | | |
| thrombomo-dulin | n.t. | 1.551 ± 0.099 | 1.625 ± 0.183 |
| injured (vehicle) | 1.759 ± 0.398 | | |
| injured (untreated) | 1.432 ± 0.188 | | |

*P < 0.05,
**P < 0.01 vs. sense treated and/or untransfected vessels.
n.t. = not tested,
vehicle = treated with HVJ complex without ODN,
N = 4–8 rats.

The invention is related to a method for inhibiting expression of protein encoding genes using antisense oligonucleotides. The method is based on the localized application of the oligonucleotides to a specific site in vivo. The oligonucleotides preferably are applied directly to the target tissue in a mixture with an implant or gel, or by direct injection or infusion. In one aspect, the oligonucleotides are modified to render them resistant in vivo to degradation or alteration by endogenous enzymes.

The therapeutic approach using antisense oligonucleotides is based on the principle that the expression of a protein from a gene can be down regulated by providing an appropriate length oligonucleotide which is complementary to at least a portion of the messenger RNA (MRNA) transcribed from the gene. The antisense strand hybridizes with the mRNA and targets the MRNA for down regulation thereby preventing ribosomal translation, and subsequent protein synthesis.

Preferred Oligomers

The Oligomer selected may be any of a number of types, including those having a charged or uncharged backbone.

Preferred Oligomers include alkyl- and aryl- phosphorate Oligomers, especially preferred are methylphosphonate Oligomers. Other preferred Oligomers include phosphorothioate Oligomers, phosphorodithioate Oligomers, morpholino analogs, formacetal analogs, thioformacetal analogs and peptide nucleic acid ("PNA") analogs.

Preferably the Oligomers each comprise from abut 4 to about 40 nucleosides, more preferably, from about 6 to 30 nucleosides. Especially preferred are Oligomers of about 8 to about 20 nucleosides.

Preferred target regions when the nucleic acid target sequence is mRNA or pre-mRNA include the 3'-untranslated region, the coding region, splice sites of pre-mRNA (including splice donor and splice acceptor sites), the initiation codon region including regions slightly downstream of the AUG start codon (preferably up to about 20 nucleotides downstream from the AUG initiation codon), regions immediately 5'- of the initiation codon (preferably about 5 to 200 nucleotides 5'- of the AUG start codon) and the 5'-cap cite.

According to an alternately preferred aspect, tandem Oligomers are employed. Preferred tandem Oligomers include those which comprise a total of about 20 to about 40 nucleosides.

Oligomers having the selected internucleoside linkages may be conveniently prepared according to synthetic techniques known to those skilled in the art. For example, commercial machines, reagents and protocols are available for the synthesis of Oligomers having phosphodiester and certain other phosphorus-containing internucleoside linkages. See also Gait, M. J., *Oligonucleotide Synthesis: A Practical Approach* (IRL Press, 1984); Cohen, Jack S., *Oligodeoxynucleotides Antisense Inhibitors of Gene Expression*, (CRC Press, Boca Raton, Fla., 1989); *Oligonucleotides and Analogues: A Practical Approach*, (F. Eckstein, 1991); and Agarwal, S., *Protocols for Oligonucleotides and Analogs Synthesis and Properties*, (Humana Press, N.J., 1993). Preparation of Oligomers having certain non-phosphorus-containing internucleoside linkages is described in U.S. Pat. No. 5,142,047, the disclosure of which is incorporated herein by reference.

Synthetic methods for preparing methylphosphonate Oligomers are described in Lee B. L., et al., *Biochemistry* 27:3197–3203 (1988), Miller, P. S., et al., *Biochemistry* 25:5092–5097 (1986), and "An Improved Method for the Synthesis and Deprotection of Methylphosphonate Oligonucleotides" in *Protocols for Oligonucleotides and Analogs Synthesis and Properties*, S. Agarwal, ed. (Humana Press, N.J. 1993); and published PCT applications WO 92/07864 and WO 92/07882 the disclosures of which are incorporated herein by reference.

Also preferred are Oligomers which are nucleoside/non-nucleoside polymers. Suitable Oligomers also include chimeric oligonucleotides which are composite RNA, DNA analogues (Inouo et al., FEBS Lett. 2115:327 (1987)). Other suitable Oligomers include Oligomers having chimeric backbones. Such chimeric backbone Oligomers include Oligomers having mixed phosphate backbones including nucleoside sequences which are capable of activating RNaseH, nucleoside sequences which do not activate RNaseH, and thus allow site directed cleavage of an RNA molecule. See U.S. Pat. No. 5,149,797 which is incorporated herein by reference. Chimeric backbone Oligomers also include Oligomers having a mixture of internucleosidyl linkages which may or may not include phosphorus atoms, such as morpholinyl linkages, formacetal linkages, peptide nucleic acid (PNA) linkages and the like. Oligomers having a neutral backbone, for example, methylphosphonate Oligomers with cleaving or cross-linking moieties attached, may prove advantageous in certain circumstances; such Oligomers may have a longer half-life in vivo since the neutral structure reduces the rate of nuclease digestion while the cleaving or cross-linking moiety may promote inactivation of target polynucleotide sequences.

According to one aspect of the present invention, these antisense Oligomers have a sequence which is complementary to a portion of the RNA transcribed from the selected target gene. Although the exact molecular mechanism of inhibition has not been conclusively determined, it has been suggested to result from formation of duplexes between antisense Oligomer and the RNA transcribed from the target gene. The duplexes as formed may inhibit translation, processing or transport of an mRNA sequence or may lead to digestion by the enzyme RNaseH.

Single stranded Oligomers may also bind to a duplex DNA target such that a duplex is formed with one of the two DNA strands, and the second DNA of the target strand is displaced from the duplex. Preferred is the formation of a duplex by the Oligomer with the coding strand of the DNA duplex target ("invading duplex"). The invading duplex so formed may inhibit transcription.

As a general matter, the Oligomer employed will have a sequence that is complementary to the sequence of the target nucleic acid. However, absolute complementarily may not be required; in general, any Oligomer having sufficient complementarily to form a stable duplex with the target nucleic acid is considered to be suitable. Since stable duplex formation depends on the sequence and length of the hybridizing Oligomer and the degree of complementarily between the antisense Oligomer and the target sequence, the system can tolerate less fidelity (complementarily) when longer Oligomers are used. However, Oligomers of about 8 to abut 40 nucleosidyl units in length which have sufficient complementarily to form a duplex having a melting temperature of greater than about 40° C. under physiological conditions are particularly suitable for use according to the method of the present invention.

Definitions

As used herein, the following terms have the following meanings unless expressly stated to the contrary.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases. In RNA, the 5-carbon sugar is ribose; in DNA, it is 2'-deoxyribose. The term nucleoside also includes other analogs of such subunits, including those which have modified sugars such as 2'-O-alkyl ribose.

The term "phosphorate" refers to the group

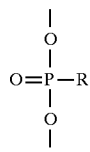

Wherein R is hydrogen or an alkyl or aryl group. Suitable alkyl or aryl groups include those which do not sterically hinder the phosphorate linkage or interact with each other. The phosphorate group may exist in either an "R" or an "S" configuration. Phosphorate groups may be used as internucleosidyl phosphorus group linkages (or links) to connect nucleosidyl units.

The term "phosphodiester" or "diester" refers to the group

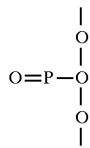

wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleotide" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleotide alkyl-and aryl-phosphorate analogs, alkyl- and aryl- phosphonothioates, phosphorothioate or phosphorodithioate analogs of oligonucleotides, phosphoramidate analogs of oligonucleotides, neutral phosphate ester oligonucleotide analogs, such as phosphotriesters and other oligonucleotide analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone or a nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "alkyl- or aryl-phosphorate Oligomer" refers to Oligomers having at least one alkyl- or aryl-phosphorate internucleosidyl linkage. Suitable alkyl- or aryl-phosphorate groups include alkyl- or aryl- groups which do not sterically hinder the phosphorate linkage or interact with each other. Preferred alkyl groups include lower alkyl groups having from about 2 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage.

The term "neutral Oligomer" refers to Oligomers which have nonionic internucleosidyl linkages between nucleoside monomers (i.e., linkages having no positive or negative ionic charge) and include, for example, Oligomers having internucleosidyl linkages such as alkyl- or aryl- phosphorate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, and carbamate linkages. Optionally, a neutral Oligomer may comprise a conjugate between an oligonucleotide or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable or cleaving a targeted portion of a nucleic acid, and the like. Such conjugation partners may further enhance the uptake of the Oligomer, modify the interaction of the Oligomer with the target sequence, or alter the pharmacokinetics distribution of the Oligomer. The essential requirement is that the Oligonucleotide or nucleoside/non-nucleoside polymer that the Oligomer conjugate comprises be substantially neutral and capable of hybridizing to its complementary target sequence.

The term "substantially neutral" in referring to an Oligomer refers to those Oligomers in which at least about 80 percent of the internucleosidyl linkages between the nucleoside monomers are nonionic linkages.

The term "neutral alkyl- or aryl- phosphorate Oligomer" refers to neutral Oligomers having neutral internucleosidyl linkages which comprise at least one alkyl- or aryl- phosphorate linkage.

The term "neutral methylphosphonate Oligomer" refers to neutral Oligomers having internucleosidyl linkages which comprise at least one methylphosphonate linkage.

The term "tandem oligonucleotide" or "tandem Oligomer" refers to an oligonucleotide or Oligomer which is complementary to a sequence located either on the 5'- or 3'-side of a target nucleic acid sequence and which is co-hybridized with a second Oligomer which is complementary to the target sequence. Tandem Oligomers may improve hybridization of these Oligomers to the target by helping to make the target sequence more accessible to such Oligomers, such as by decreasing the secondary structure of the target nucleic acid sequence. In addition, one member of a pair of tandem Oligomers may improve the hybrid stability of the second tandem Oligomer to the target nucleic acid sequence by promoting a helical structure at either the 5'- or 3'- end of said second Oligomer and vice-versa.

A preferred therapy is a combination of antisense molecules targeted against a cyclin and a cyclin dependent kinase. By "antisense molecules against", "antisense sequences against", "antisense against", and similar terms is meant an oligomer complementary to a nucleic acid target sequence for a particular cyclin or cyclin dependent kinase which oligomer will prevent or interfere with expression or function of the particular cyclin or cyclin dependent kinase. Certain combinations of cyclins and cyclin dependent kineses that are reported to be involved in smooth muscle proliferation and restenosis. In the transition of cells from G1 to S-phase, the early stages of smooth muscle proliferation in response to injury in the vessel wall, the kinase cdk2 is reported to be activated by a combination of cyclins A and E which appear late in G1 (Koff, et al., Science, 1992 257:1689). Accordingly, a combination preferred of antisense molecules to decrease or inhibit restenosis would be either a combination of antisense oligomers against cyclin A and cdk2 or cyclin E and cdk2. Cyclin P46 or cyclin X (Williams et al. J. Biol. Chem., 1993 268:8871) has been reported to appear in mid G1 and to activate cdk2 ahead of cyclins A and E. Thus, another preferred combination would be the combination of antisense against cyclin X and cdk2. The cell cycle dependent kinase cdk4 has been reported to be activated earlier in G1 than in cdk2, and appears to be important in the G1-S-phase transition. Cdk4 has been reported to be activated by the inductions of cyclins D2 and D3. (Matsushime, et al. Cell, 1992. 71:323). We believe the combinations of antisense sequences against D2 and cdk4, or D3 and cdk4 are also preferred.

Once cells pass through the G1-S-phase transition and replicate their DNA, they are termed "competent". Cell division can be inhibited by preventing synthesis or conversely by inhibiting the later stage transition from G2 to M-phase termed "mitosis". Cdc2 controls "progression" and it is activated by complexing with the cyclins B1, B2, and A. (Parker and Pinwoica-Worms, Science, 1992. 257:1955). Thus, a preferred combinations of antisense oligomers to inhibit mitosis would be a cyclin B-cdc2, or a cyclin A-cdc2. Since the induction of cyclins has been reported as a key event in activation of cyclin-kinase complex leading to transition of cells into and through the cell cycle (Ohtsubo and Roberts, Science, 1993, 259:1908). Cyclins D-type, D2 and D3 which have been reported to activate cdk4 (Ajchenbaum et al., J. Biol. Chem., 1993, 268:4113) are reported to be induced by growth factors. Accordingly, antisense oligomers to these proteins may be employed according to the methods of the present invention.

The net effect of induction of cyclins is the activation of the nuclear kinase complexes leading to phosphorylation of nuclear proteins and then liberation of free transcription factors such as E2F that promote expression of genes that are important in replication of DNA and mitosis. O'Connor et al. (J. Biol. Chem., 1993. 268:8298) have reported that the nitrogen mustard drugs, known inhibitors of cell division, work by specifically interfering with the cyclin A-cdk2 complex and the cyclin B1-cdc2 complex. It is believed that combinations of antisense molecules which interfere with the cyclin A-cdk2 complex will prevent DNA synthesis and molecules that interfere with the cyclin B1-cdc2 complex will interfere with mitosis.

A preferred combination is an antisense sequence against proliferating cell nuclear antigen (PCNA) and an antisense sequence to cyclin or a cyclin dependent kinase and most particularly an antisense sequence against PCNA and cdc2. Antisense sequences complimentary to the mRNA of the proteins that express basic fibroblast growth factor (bFGF), transforming growth factor-beta (TGF-β), and platelet derived growth factor (PDGF) alone or in combination with the above cyclins or cyclin dependent kinases are useful in practicing this invention.

Methods of Application of the Oligonucleotides

The antisense sequences may be administered in any convenient vehicle, which is physiologically acceptable. For the most part liquid media will be employed, such as saline, phosphate buffered saline, aqueous ethanol, or other media composition compatible with the oligomers and the tissue or cells to be treated. In some instances liposomes may be employed to facilitate uptake of the antisense oligonucleotide into the target vascular smooth muscle cells, particularly where the liposome is bound to ligands for target cell receptors, which provide for endocytosis of the subject compositions. Hydrogels may also be used as depots for placement at the site of the lesion. See, for example, WO 93/01286.

Of particular interest is the use of cationic liposomes for use in cationic liposome-mediated transfection (lipofection) (see Itoh, et al. Hypertension 16, 325 (abstract) (1990)) or neutral liposomes. Concentrations of liposome will generally range from about 1–5, preferably 2–4 µg/ml in the medium, where the ratio of liposome to DNA will generally be about 1:3–1:10 (w/w), preferably about 1:6 (w/w). Neutral liposomes also find application, where mono or diester glycerides (fatty acids of from 8–24 carbon atoms, saturated or unsaturated), particularly phosphatidyl serine, phosphatidyl choline, etc., cholesterol, or other neutral liposome-forming monomers may find use. Moreover, complexing or covalent binding to the liposomes of proteins which aid in the binding and uptake of the liposomes find use, such as viral coat proteins, monoclonal antibodies to surface membrane proteins, and the like. The manner of binding and the particular proteins will vary depending on the target tissue, manner of administration, protein availability, stability, level of immunogenicity and the like.

The invention is useful in preventing proliferation of smooth muscle cells in a variety of vascular procedures such as coronary artery angioplasty, renal artery angioplasty, carotid artery surgery, renal dialysis fistulae stenosis, and vascular graft stenosis.

The antisense sequence is in a pharmaceutically acceptable compositions and is applied directly to the vascular site of injury.

Kato, et al., The Journal of Biological Chemistry, Vol. 266, No. 6, Feb. 25, pp. 3361–3364 (1991), Kaneda et al., Science, Vol. 243 pp. 375–378 (1988) describe liposomes containing the hemagglutinating virus of Japan (HVJ) as a vehicle for delivering DNA to cells. The HVJ containing liposomes have been found to be particularly useful vehicles for localized delivery of the antisense sequences of this invention.

Whenever possible, administration of the subject compositions will be localized, either by virtue of cell surface recognition markers, or by the manner of administration, such as catheter, syringe, placement of a depot, and the like. In some instances, the subject compositions may be infused upstream from the site of the cells whose activity is to be modulated. The agent can be introduced to the vessel wall luminally, intramurally or periadventitially to localize the agent at the site of the lesion. One preferred method is to deliver the antisense drug through a catheter placed in the coronary artery at the site of the lesion following the angioplasty. The localized concentration or amount administered may be determined empirically and will depend upon the purpose of the administration, the area to be treated, the effectiveness of the composition, the manner of administration, and the like. The local concentration will desirably be in the range of about 0.1 to 50 μM.

The following examples are offered by way of illustration and not by way of limitation of the present invention.

EXPERIMENTAL

Example 1

Growth of Vascular Smooth Muscle Cells in Culture

Rat aortic smooth muscle cells (passage 5–10) isolated and cultured according to the method of Owens, et al. (*J. Cell. Biol.*, 102, 343–352 [1986]), were plated into 24-well culture dishes at $1\times10^4$ cells/well. At confluence, the cells were made quiescent by incubation for 48 hours in a defined serum-free (DSF) medium containing insulin ($5\times10^{-7}$M), transferrin (5 μg/ml), and ascorbate (0.2 mM). This growth condition maintains smooth muscle cells in a quiescent, non-catabolic state and promotes the expression of smooth muscle cell-specific contractile proteins.

Synthesis and Purification of Oligomers

Oligonucleotide sequences utilized in this study and their relationships to TGF-$\beta_1$, bFGF, and PDGE A chain mRNAs (Sporn, et al., *J. Cell Biol.* 105, 1039–1045 [1987]; Burgess and Maciag, *Ann. Rev. Biochem.* 58, 575–606 [1989]; Betsholz, et al., *Nature* 320, 695–699 [1986] are shown below.

Unmodified, 15-base deoxyribonucleotides were synthesized on an automated solid-phase synthesizer (Applied Biosystems Incorporated) using standard phosphoramide chemistry. Prior to use, the oligomers were purified by gel filtration, ethanol-precipitated, lyophilized to dryness and dissolved in the culture media. Antisense TGF, antisense FGF and antisense PDGF oligonucleotides were complementary to human TGF-$\beta_1$ mRNA, bFGF and MRNA, and PDGR A chain mRNA, respectively, at the translation initiation region. Control oligonucleotides were either the sense oligonucleotide (sense TGF, sense FGF, sense PDGF) or the oligonucleotide with the same oligonucleotide sequence but with a reversed 5'-3' orientation (reverse TGF, reverse FGF). To introduce the oligonucleotides into VSMC, a cationic liposome-mediated transfection method (lipofection) was employed (Itoh, et al. *Hypertension* 16, 325 [abstract] [1990]; Nabel, et al., *Science* 249, 1285–1288 [1990]). Oligonucleotides dissolved in 50 μl DSF media were mixed with Lipofectin™ Reagent DOTMA (N[1-(2,3-dioleyloxy)propyl]-N,N,N-trimethylammonium chloride) (BRL Life Technologies, Gaithersburg, Md.) dissolved in the same volume of water in a ratio of 6/1 (w/w) and incubated for 30 minutes at room temperature. The oligonucleotides/lipsome complex (100 μl) was then added dropwise to each well.

Bioassay for TGF-β

CCL-64 mink lung epithelial cells (Danielpour, et al., *J.Cell. Physiol.* 138, 79–86 [1989] were maintained in MEM supplemented with 10% fetal calf serum and 0.1 mM nonessential amino acids. Cells were spread at a density of $4\times10^4$ cells/well in 24-well plates one day before the assay. The subconfluent cells were washed once and fed with DSF containing vehicle or TGF-β (human TGF-$\beta_1$, R & D Systems, Minneapolis, Minn.). Twenty hours later, the cells were pulsed for 8 hours with $^3$H-thymidine (10 μCi/ml). The incorporation of $^3$H-thymidine was determined as described below and expressed as the percent of incorporation of the control (without TGF-β) wells. The levels of TGF-β, secreted from quiescent VSMC in a 14-hour period were similarly assayed at four dilutions.

Demonstration that the inhibitory effects of the conditioned media were due to TGF-β was accomplished by blocking the growth inhibitory effect with a neutralizing antibody. Fresh DSF media, human TGF-$\beta_1$ (2 ng/ml) in DSF media, or the conditioned media collected from VSMC were incubated at 37° C. for 1 hour with either turkey preimmune serum or turkey anti-human TGF-$\beta_1$ antiserum (Danielpour, et al., 1989, supra) (1/200 final dilution prior to the addition to the CCL-64 mink lung epithelial cell bioassay at a 1/2 dilution. This treatment completely abolished the growth inhibitory action of the conditioned media (Gibbons, et al., *Clin. Res.* 38, 287a [1990]).

Bioassay for bFGF

Extraction of bFGF from VSMC and bioassay for bFGF activity using mouse 3T3 fibroblasts were performed as in a previous report (Klagsbrun, et al., *Proc. Natl. Acad. Sci. USA* 83. 2448–2452 [1986]). Confluent quiescent rat VSMC ($1.3\times10^{-7}$) with or without previous treatment with anti-sense FGF-oligonucleotides were harvested from monolayer cultures by trypsinization, washed with phosphate-buffered saline, (1 μg/ml), pepstatin (4 μM) and phenylmethylsulfonyl fluoride (1 nM). After cells were disrupted by 3 cycles of freezing and thawing followed by sonication for 1 minute, the homogenate was centrifuged at 25,000×g for 30 minutes and the supernatant was dialyzed overnight against 0.1M NaCl/0.01M Tris-HCl, pH 7.5. All procedures were performed at 4° C., and aliquots of cell extracts were stored at −80° C. until use. For the measurement of bFGF activity, human bFGF standards 0.03–3 ng/ml, Genzyme Corporation, Boston, Mass.) or samples pre-incubated (2 hours at 37° C.) with either anti-bFGF IgG (R & D Systems, Minneapolis, Minn.) or non-immune IgG at 10 μg/ml were incubated with quiescent Swiss 3T3 cells for 20 hours, after which the cells were pulse-labeled with 10 μCi/ml $^3$H-thymidine for 8 hours. Addition of non-immune IgG had no effect on basal or bFGF-stimulated thymidine incorporation, nor did the administration of anti-bFGF IgG affect basal thymidine uptake. Anti-bFGF IgG (10 μg/ml) almost completely abolished the mitogenic activity of 1 ng/ml recombinant human bFGF, without affecting the mitogenic activity of acidic FGF or PDGF. Serial dilution curves of cell extracts were parallel to the standard curve of bFGF, and cellular bFGF content was estimated by antibody-suppressible mitogenic activity in the samples.

Determination of DNA Synthesis

Relative rates of DNA synthesis were assessed by determination of tritiated thymidine (10 μCi/ml) incorporated into trichloracetic acid (TCA)-precipitable material as previously reported (Itoh, et al., *J. Clin. Invest.* 86, 1690–1697 [1990]).

Results

Ang II was shown to induce a 2.5-fold increase in the VSMC synthesis and release of biologically-active TGF-β using the mink lung epithelial cell bioassay. In this assay, active TGF-β caused a dose-dependent inhibition of DNA synthesis of the cells ($IC_{50}=8\times10^{-11}$M). The growth inhibitory activity in the conditioned media of the VSMC could be abolished by prior incubation of the media with a specific TGF-β neutralizing antibody. This demonstrated the specificity of the assay for TGF-β.

The synthesis by VSMC of bFGF was shown to be stimulated by Ang II. Messenger RNA for bFGF was induced modestly by Ang II (approximately 2-fold), while antibody-inhibitable bFGF activity in cell extracts, as detected by the Swiss 3T3 cell bioassay was increased 3-fold. In this assay, confluent, quiescent VSMC are exposed to vehicle (basal) or Ang II ($10^{-6}$M) and the cells extracted and assayed for antibody-inhibitable bFGF activity using Swiss 3T3 fibroblasts as bioassay. The standard curve demonstrated the dose-dependent simulation of DNA synthesis by bFGF. Extracts from Ang II-treated cells contained 2–3-fold higher bFGF activity.

Antisense oligonucleotides (15 mer) complementary to human TGF-$\beta_1$ bFGF and PDGF A chain mRNAs as well as control oligonucleotides were synthesized. See FIG. 1.

The oligonucleotides were introduced into VSMC by cationic liposome-mediated transfection (lipofection). The optimum in vivo concentration of cationic liposome and its ratio to DNA that minimized cell toxicity and optimized DNA uptake were determined to be 2–4 $\mu$g/ml and 1:6 (w/w), respectively.

To determine the effect of antisense oligonucleotides on the production of TGF-$\beta$ and bFGF, confluent quiescent VSMC were treated with antisense or control oligonucleotides (5 $\mu$M) directed against TGF-$\beta$ or bFGF. 50 and 250 $\mu$l of conditioned media were collected after 20 h and assayed for TGF-$\beta$ activity using the mink lung epithelial cell bioassay. Antisense oligonucleotides resulted in a 75% decrease in TGF-$\beta$ activity. bFGF content in extracts of control or antisense oligomer-treated VSMC was assayed using the Swiss 3T3 bioassay. The antisense oligomer inhibited bFGF production by 85%.

Extracts from quiescent VSMC contained 2.9 ng of bFGF per mg protein. This quantity was unaffected by incubation with control oligonucleotide but was decreased to below detectable levels (<1 ng/mg protein) when the cells were incubated with 4 $\mu$M antisense oligomer for 24 h.

In a companion study, the growth of cultured endothelial cells, which utilized bFGF as an autocrine growth factor, was also inhibited effectively with antisense oligomers directed against bFGF.

In the next study, the effects of the antisense TGF-$\beta$ oligonucleotide on DNA synthesis in basal and Ang II-stimulated VSMC were determined. The effect of antisense oligomers on VSMC proliferation was determined by transfecting confluent quiescent VSMC with antisense or control oligonucleotides (5 $\mu$M) 4 hours prior to addition of vehicle or Ang II ($10^{-6}$M). After 20 hours, the cells were labeled with 10 $\mu$Ci/ml $^3$H-thymidine for 8 hours. Thymidine incorporation was then determined by measuring the radioactivity of the cells. TGF-$\beta$ antisense oligomer (5 $\mu$M) potentiated DNA synthesis by 35% in basal state, but more significantly in Ang II-stimulated state (87%, p>0.05). In contrast, there was no change in the rate of DNA synthesis in Ang-II-stimulated cell groups transfected with the control oligomer. The results indicate that TGF-$\beta$ exerts a tonic inhibitory action on VSMC proliferation and that in the Ang II-stimulated state, it plays an even greater role in growth inhibition. The antisense TGF treatment also causes a significant reduction of RNA synthesis ($^3$H-uridine incorporation) by 60% at the basal state. These results support the conclusion that endogenous production of TGF-$\beta$ exerts a hypertropic and antiproliferative action.

The effect of the antisense oligomer to bFGF employed at 5 $\mu$M was shown to suppress DNA synthesis in the basal state and inhibited this process significantly by (30%) in the Ang II-stimulated state. bFGF acts as a promoter of VSMC proliferation, especially in the Ang II-stimulated state. In contrast, antisense oligomers directed against PDGF-A had no effect on basal or Ang II-stimulated $^3$H-thymidine incorporation. The data supports the conclusion that Ang II activates a growth-stimulatory pathway mediated primarily by bFGF.

Co-transfection of bFGF antisense oligomer with TGF-$\beta$ antisense oligomer almost completely abolished Ang II-induced VSMC proliferation. The co-transfection of bFGF antisense oligomer with TGF-$\beta$ antisense oligomer almost completely abolished Ang II VSMC proliferation that was unmasked by the blockade of TGF-$\beta$ production. In contrast, transfection of the antisense directed against PDGF-A had no effect on the DNA synthesis uncovered by the antisense oligomer directed against TGF-$\beta$.

The above data supports the conclusion that the bFGF and TGF-$\beta$ growth factor counteract within the same population in an autocrine and/or intracrine fashion. Since bFGF is known to promote the production of plasminogen activator, which is crucial for the activation of TGF-$\beta$, the interaction of these dual autocrine loops in the production and activation of these growth factors is an essential aspect of the regulation of VSMC proliferation.

Example 2

Confluent, quiescent cells, cultured as described in Example 1, were exposed to a combination of antisense oligomers directed against cdc2 kinase, cdk2 kinase, and cyclin B (Tables 2 and 3) (4 $\mu$M each). The oligomers were synthesized as described above with the exception that phosphorothiate modified nucleotides were employed. The oligomers (antisense and control) were introduced into the cells using virally mediated liposome uptake (Kaneda, et al., J. Biol. Chem., (1989) 264, 12126–12129). To assess the effect of these oligomers on the growth of VSMC, cells were grown for 4 days after oligomer exposure. The cells were then harvested by trypsin and assayed for DNA content. The results demonstrated that sense oligomer treated cultures had DNA contents indistinguishable from control untreated cultures, demonstrating that the sense oligomers had no effect on the basal growth of the VSMC cultures. On the other hand, cells exposed to the antisense oligomers exhibited a 50% decrease in DNA content, demonstrating that these oligomers decreased by 50% the basal growth of these cultures.

These oligomers also inhibited growth factor stimulated growth. Treatment of these cells with FGF increased the content of DNA by 4-fold. In cultures treated with FGF plus sense oligomers, DNA content increased 3-fold, demonstrating that the presence of sense oligomers had little effect on growth factor-induced increase in DNA content. However, when FGF-treated cells were exposed to the antisense oligomers, no increase in the basal levels of DNA were observed, demonstrating that these oligomers blocked the growth factor induced growth of these cells.

Similar results were seen when a combination of antisense oligomers directed against cdc2 kinase and PCNA were used.

Example 3

HVJ-Liposome Preparation

Briefly, HVJ-liposomes useful in the instant invention may be prepared, for example, by the following procedure. First an appropriate weight of phosphatidylserine, phosphatidylcholine, and cholesterol are mixed in a weight ratio of 1:4.8:2 and dried (for example 10 mg total lipid). The dried lipid mixture is then hydrated in 200 $\mu$l of balanced salt solution (BSS; 137 mM NaCl, 5.4 mM KCl, 10 mM Tris-HCl, pH 7.6) containing sense or anti-sense-ODN (120 nmol). Liposomes are then prepared by shaking and sonication of the rehydrated mixture such that the liposomes form.

Purified HVJ (Z strain) is inactivated by UV irradiation (for example 110 erg/mm$^2$/sec) for about 3 minutes just before use. The liposome suspension (about 0.5 ml, containing 10 mg lipids) is then mixed with the irradiated HVJ (about 1000 hemagglutinating units) in a total volume of about 4 ml BBS. This mixture is incubated at 4° C. for about 5 minutes then for 30 minutes with gentle shaking at 37° C. during which HVJ becomes associated with the liposomes. Free HVJ is removed from the mixture of newly formed HVJ-liposomes by sucrose density gradient centrifugation.

This same general procedure applies to the later examples.

Growth of Vascular Smooth Muscle In Vivo in Response to Injury

Male Sprague-Dawley rats weighing 500–550 grams were used. Endothelial denudation and injury to the vascular wall were performed on carotid arteries. Rats were anesthetized with the administration of kentamine hydrochloride (80 mg/kg) (Parke-Davis, Morris Plains, N.J.) and xylazine (12 mg/kg) (Lloyd Laboratories, Shenandoah, Iowa). A 2 French embolectomy balloon catheter (American Edward Laboratories, Santa Ana, Calif.) was passed into the left common carotid via the left external carotid artery according to the previously described method of Clowes, et al. (Lab Invest. 49, 208–215 [1983]). Using Evans Blue staining, we documented that this procedure denuded the endothelium effectively. The right, uninjured carotid was used as a control.

At the time of injury, some animals received a combination of antisense oligomers directed against cdc2 kinase and PCNA (tables 2 and 3). The synthesis of the oligomers was as described above except that phosphothionate modified sequences were employed. The oligomers were introduced lumenally to the vessel wall. Uptake of the DNA was mediated via virally coated liposomes (Kaneda, et al., J. Biol. Chem. 264, 12126–12129 [1989]).

To determine the effect of the oligomer treatment on DNA synthesis in the injured vessel, the animals were injected with BrdUr. This thymidine analogue is incorporated into the newly synthesized DNA and is detected immunohistochemically.

All rats were euthanized 4 days following injury. Rats were anesthetized and blood was withdrawn from the ascending aorta via the left verticle. The rats were then perfused at a pressure of 110 mm/Hg through the ascending aorta with 100 ml of phosphate buffered saline (PBS, pH 7.2). The carotid arteries were removed and small segments were fixed in 10% formaldehyde and embedded in paraffin. Five micron sections were cut on a rotary microtome and placed on glass slides that had been treated for 20 seconds with acetone containing 2% 3-aminopropyltriethoxysilane (Sigma Chemical, St. Louis, Mo.). The sections were digested with 0.1% trypsin (Sigma Chemical, St. Louis, Mo.) in PBS at 37° C. for 12 minutes. The sections were then preincubated with normal serum from the species that the second step antibody was produced. The sections were then covered with a primary antibody specific for BrdUr, incubated for 15 minutes at 4° C., washed with PBS and then incubated with the biotinylated secondary antibody. After washing, the sections were incubated with avidinbiotinylated horseradish peroxidase complex (Vectastain ABC kits, Vector Laboratory, Burlingame, Calif.), and developed with 0.1% diaminobenzidine tetrahydrochloride (Aldrich Chemical, Milwaukee, Wis.) and 0.02% $H_2O_2$ (Sigma Chemical, St. Louis, Mo.), the slides were then counter stained with hematoxylin. Positive staining appeared as brown in color. Negative controls included the following: 1) omission of primary or secondary antibody, 2) replacement of the primary antibody by non-immune serum or immunoglobulin of the same species.

The results demonstrated that control uninjured vessels exhibit very low levels of DNA synthesis (<1% BrdUr labeling index). On the other hand, the injured untreated vessel inhibited a high level of BrdUr staining (23% BrdUr labeling index) demonstrating that vascular injury induces DNA synthesis within the vessel wall. In the cases of exposure of these injured vessels to antisense oligomers, DNA synthesis was decreased by 60%. Moreover, DNA content within the antisense treated vessel wall decreased by 40% when compared to the sense treated vessel.

Neointima formation was assessed by morphometry of perfusion-fixed specimens 14 days after balloon injury in a blinded fashion. Our results demonstrated a dose-dependent suppression of neointima formation by the combination of PCNA-cdc2 antisense oligodeoxynucleotide (ODN). A low dose (3 $\mu$M each) of antisense ODN inhibited neointima formation by approximately 60% (n=7) compared to vessels treated with the HVJ-liposome complex alone (n=5) or sense ODN-treated vessels (n=8). The antisense ODN had no significant effect on medial area. At a dose of 15 $\mu$M each, a single administration of the PCNA-cdc2 antisense ODN combination completely abolished neointima formation (n=8), (greater than 95%) whereas sense control ODN had no effect (n=8) FIG. 3. Importantly, a significant inhibition of neointima formation was observed up to 4 and 8 weeks after administration of the PCNA-cdc2 antisense ODN combination compared to sense control, FIG. 3. Intraluminal transfection of PCNA antisense ODN alone failed to inhibit neointima formation (neointimal area=0.237 ±0.016 mm$^2$ versus sense control area=0.214±0.022 mm$^2$, p. 0.05). These data suggest that there is an amplified inhibitory effect of combined administration of both PCNA and cdc2 antisense ODN. The selectivity of the antisense ODN effect was further confirmed by the observation that the inhibition of the neointima was limited to the area of intraluminal transfection. In contrast, the adjacent injured carotid segments outside the area of antisense transfection exhibited neointimal lesions similar to the sense ODN-treated control. These results are summarized in FIG. 3.

The intraluminal administration of antisense cdk2 alone at 3 $\mu$M and 15 $\mu$M with the HVJ method resulted in a 60% reduction in DNA synthesis as measured by BrdUr labeling as well as a 60% reduction in neointima lesion formation at 2 weeks after vascular injury (FIG. 4, columns 4 and 6). As can be seen from FIG. 4, column 5, the effect of administering the combination of cdk2 antisense ODN (3 $\mu$M) and cdc2 (3 $\mu$M) antisense ODN on neointima formation was not significantly different from cdk2 (3 $\mu$M) alone.

Since DNA synthesis in the cell of the injured vessel is required for full development of the neointimal lesion, inhibition of DNA synthesis in those cells should inhibit the lesion formation.

The above concentrations of antisense sequences to PCNA and cdc2 were conveniently used to demonstrate the synergistic effect of these sequences on modifying DNA synthesis and cardiovascular cellular activity of vascular smooth muscle cells associated with formation of neointima. The desired range of antisense concentration can be determined empirically for difference antisense sequences and will vary depending on factors such as, but not limited to, the nature and location of the sequence targeted by the antisense and the length of the antisense sequence.

Example 4

This example summarizes a study performed in an attempt to enhance the efficiency of cellular uptake and the stability of antisense ODN. The study involves a viral protein-mediated ODN transfer technique.

Synthesis of oligomers and selection of sequence targets

The sequences of antisense oligonucleotides (ODN) against cell cycle regulatory genes used in this Example are shown in Table 4. Synthetic ODN were washed by 70% ethanol, dried, and dissolved in sterile Tris-EDTA buffer (10 mM Tris, 1 mM EDTA.) The supernatant was purified over NAP 10 column (Pharmacia), and quantitated by spectrophotometry as described in Itoh, J., Mukoyama, M., Pratt, R. e., Dzau, V. J. (1992) Biochem Biophysic Res Comm 188, 1205–1213.

Preparation of HVJ-liposomes

Phosphatidylserine, Phosphatidylcholone, and cholesterol were mixed in a weight ratio of 1:4.8:2 as described in Kaneda, Y., Iwai, K., Uchida, T. (1989) Science 243, 375–378; Tomita, N., Higaki, J., Morishita, R., Kato, K., Mikami, J., Kaneda Y., Ogihara, T. (1992) Biochem Biophysic Res Comm 186, 129–134; Morishita, R., Gibbons, G. H., Kaneda, Y., Ogihara, T., Dzau, V. J., J Cell Biochem; Itoh, J., Mukoyama, M., Pratt, R. e., Dzau, V. J. (1992) Biochem Biophysic Res Comm 188, 1205–1213. Dried lipid was hydrated in 200 $\mu$l of balanced salt solution (BSS; 137 mM NaCl, 5.4 mM KCl, 10 mM Tris-HCl, pH 7.6) containing sense or antisense-ODN (600 nmol). Liposomes were prepared by shaking and sonication. Purified HVJ (Z strain) was inactivated by UV irradiation (110 erg/mm$^2$/sec) for 3 min just before use. The liposome suspension was mixed with HVJ (10000 hemagglutinating units) in a total volume of 4 ml of BSS. The mixture was incubated at 4° C. for 5 minutes and then for 30 minutes with gentle shaking at 37° C. Free HVJ was removed from the HVJ-liposomes by sucrose density gradient centrifugation. The top layer of the sucrose gradient was collected for use. The final concentration of antisense ODN is equivalent to 15 $\mu$M, as calculated according to Kaneda, Y., Iwai, K., Uchida, T. (1989) Science 243, 375–378; Tomita, N., Higaki, J., Morishita, R., Kato, K., Mikami, J., Kaneda Y., Ogihara, T. (1992) Biochem Biophysic Res Comm 186, 129–134; Morishita, R., Gibbons, G. H., Kaneda, Y., Ogihara, T., Dzau, V. J., J Cell Biochem.

In vivo transfer of ODN

A 2 French Fogarty catheter was used to induce vascular injury in male Sprague-Dawley rats (400–500 g; Charles River Breeding Laboratories) as described in Rakugi, J., Jacob, J. K., Krieger, J. E., Ingelfinger, J. R., Pratt, R. E., (1993) Circulation 87, 283–290. The rats were anesthetized, and a cannula introduced into the left common carotid via the external carotid artery. After vascular injury of the common carotid, the distal injured segment was transiently isolated by temporary ligatures. The HVJ-liposome complex was infused into the segment and incubated for 10 minutes at room temperature. After a 10 minute incubation, the infusion cannula was removed. Following the transfection, blood flow to the common carotid was restored by release of the ligatures. No adverse neurological or vascular effects were observed in any animal undergoing this procedure.

At 2, 4 and 8 weeks after transfection, rats were sacrificed and vessels were perfusion-fixed with 4% paraformaldehyde. Three individual sections from the middle of transfected segments were analyzed. In addition, three sections from the middle section of the injured untransfected region was also analyzed. Animals were coded so that the operation and analysis were performed without knowledge of which treatment individual animals received.

A statistical analysis of the results is found in Table 5. All values are expressed as mean±SEM. All experiments were repeated at least three times. Analysis of variance with subsequent Duncan's test was used to determine significant differences in multiple comparisons. P<0.05 was considered significant.

Initially, the effect of a single antisense ODN at 15 $\mu$M on the inhibition of neointima formation in rat carotid artery model was examined. Administration of either antisense cdc 2 kinase (both mouse and rat sequences) or antisense cdk 2 kinase ODN resulted in the partial inhibition of neointima formation after balloon injury, whereas antisense PCNA ODN alone failed to show any inhibitory effects. To achieve the further inhibition a combination of these ODN were administered. Indeed, a single administration of 15 $\mu$M of the PCNA/cdc 2 (mouse sequence) antisense ODN combination completely abolished neointima formation (n=8), whereas the sense control ODN (15 $\mu$M each) had no effect (n=8). The antisense ODN had no significant effect on medial area. The administration of combination of cdc 2 (rat sequences) and PCNA ODN inhibited neointima formation almost completely.

Also examined was the combination of antisense cdc 2 and cyclin B ODN. A single administration of combination of antisense cdc 2 and cyclin B ODN inhibited neointima formation significantly. The selectivity of the antisense ODN effect was further confirmed by the observation that the inhibition of the neointima formation was limited to the area of intraluminal transfection along the injured carotid artery. (FIG. 4). In contrast, the adjacent injured carotid segments outside the area of antisense transfection exhibited neointimal lesions similar to the sense ODN-treated control injured carotid artery. Transfection of antisense thrombomodulin ODN also failed to show any inhibitory effects on neointima formation, these results summarize Table 5.

The single administration of 15 $\mu$M of the PCNA/cdc 2 antisense ODN combination significantly inhibited the extent of neointima formation for a period of 8 weeks after transfection (FIG. 5). Although there was evidence for a neointimal lesion at 4 weeks after antisense treatment, the lesion was significantly inhibited as compared to sense treatment (P<0.01). Furthermore, no further progression of the lesion was observed at 8 weeks after a single antisense administration.

The results of this example indicates that neointima lesion formation after balloon angioplasty can be prevented by a single intraluminal administration of antisense oligonucleotides directed against cell cycle regulatory genes. This therapeutic strategy fulfills the criteria needed for success, i.e., a proper drug target, an efficient drug delivery method and an intraluminal approach.

In defining the strategy to prevent restenosis in humans, the method of drug delivery is critically important. Intraluminal delivery is desirable since it can be carried out concomitantly with the transluminal angioplasty—a practical issue of clinical relevance. The blockade of cell cycle progression is particularly attractive since it maintains the cells in a quiescent, differentiated phenotype without inducing cell injury. The HVJ-ODN intraluminal method described in the above example substantially increases the efficiency of uptake and the stability of ODN in vivo thereby avoiding the potential toxicity of high concentrations of ODN (i.e. >150 uM). The modification of antisense ODN pharmacokinetics by use of the HVJ-liposome complex will facilitate the potential clinical utility of these agents by: 1) allowing for an abbreviated intraluminal incubation time to preserve organ perfusion, 2) prolonging the duration of biological action, 3) enhancing specific activity.

Example 5

This example examines the fate of antisense oligodeoxynucleotides (ODN) in vivo using high efficient viral mediated transfer method (HVJ). Direct transfer of unmodified FITC-labeled ODN showed fluorescence in the medial layer, and disappeared within 1 day. In contrast, transfected unmodified FITC-ODN by HVJ method showed much florescence in the medial layer, and florescence continued at least 1 week (and disappeared within 2 weeks). Moreover, transfer of phosphorothioate FITC-ODN enwrapped in liposomes without HVJ particle resulted in a short existence of florescence (within 4 days), while transfer by HVJ method result in continuous florescence up to 2 weeks after transfection. Given that the HVJ method prolonged the half-lives of ODN the efficiency of antisense phospohorothioate ODN against cdk kinase gene to balloon injury rat carotid artery was also examined. The specificity of antisense cdk 2 ODN was confirmed by the observation that mRNA of cdk 2 in injury vessels was markedly diminished by the antisense ODN treatment. At 2 weeks after transfection, antisense cdk 2 ODN treatment resulted in a significant inhibition in neointima formation, while sense ODN treatment and untreatment did not result in reduction. On the other hand, administration of antisense cdc 2 ODN also partially inhibited neointima formation. Moreover, a single intraluminal administration of combination of antisense cdc 2 and cdk 2 ODN showed further neointima inhibition as compared to antisense cdc 2 ODN alone. This example demonstrates that a single intraluminal administration of antisense ODN directed cell cycle regulatory genes such as cdc 2 and cdk 2 with HVJ method prevented neointima formation after balloon angioplasty in rat carotid injury model via a catheter delivered system.

Synthesis of oligomers and selection of sequence targets

The sequences of ODN against human cdk 2 used in this study was following: antisense: 5'-GAA-GTT-CTC-CAT-GAA-GCG-3' (SEQ ID NO:41), sense: 5'-CGC-TTC-ATG-GAG-AAC-TTC-3' (SEQ ID NO:40) (−6−+12 of human sequence; these sequences are no different between mouse and human cdk 2). This antisense ODN specifically inhibit cdk2 protein synthesis and serum stimulated growth in rat VSMC. Also synthesized were sense and antisense cdc 2 ODN (antisense: 5'-GTC-TTC-CAT-AGT-TAC-TCA (SEQ ID NO:37), sense: 5'-TGA-GTA-ACT-ATG-GGA-GAC-3' (SEQ ID NO:36), −9 to +9 of mouse sequence), as described in Furukawa, U., Piwnica-Worms, H., Ernst, T. J. Kanakura, Y., Griffin, JJ.D. (1990) Science 250, 805–808. Synthetic ODN were purified over NAP 10 column (Pharmacia), and quantitated by spectrophotometry.

Preparation of HVJ-liposomes

Phosphatidylserine, Phosphatidylcholone, and cholesterol were mixed in a weight ratio of 1:4.8:2. Dried lipid was hydrated in 200 µl of balanced salt solution (BSS; 137 nM NaCl, 5.4 nM KCl, 10 mM Tris-HCl, pH7.6) containing sense of antisense-ODN (120 nmol). Control group was used as no ODN (BSS 200 ul). Liposomes were prepared by shaking and sonication. Purified HVJ (Z strain) was inactivated by UV irradiation (100 erg/mm²/sec) for 3 min just before use. The liposome suspension (0.5 ml, containing 10 mg of lipids) was mixed with HVJ (10000 hemagglutinating units) in a total volume of 4 ml of BSS. The mixture was incubated at 4° C. for 5 min and then for 30 min with gently shaking at 37° C. Free HVJ was removed from the HVJ-liposomes by sucrose density gradient centrifugation. The final concentration is equivalent to 3 µM. In this study, the preparation of HVJ complex was optimized to achieve the maximum effect of antisense ODN in VSMC.

In vivo gene transfer

A 2 French Fogarty catheter was used to induce vascular injury in male Sprague-Dawley rates (400–500 g; Charles River Breeding Laboratories). These rats were anesthetized with ketamine, and the left common carotid artery was surgically exposed. A cannula was introduced into the common carotid via the external carotid artery. In vivo gene transfer was assessed under following condition: Vascular injury of the common carotid was induced by the passage and inflation of a balloon catheter through an arteriotomy in the external carotid artery three times. The injured segment was transiently isolated by temporary ligatures. The HVJ-liposome complex, liposome complex without HVJ particles, or ODN alone was infused into the segment and incubated for 10 minutes at room temperature as described above. After a 10 minute incubation, the infusion cannula was removed. Following the transfection, blood flow to the common carotid was infusion by release of the ligatures, and the wound was then closed. No adverse neurological or vascular effects were observed in any animal undergoing this procedure.

In vivo transfection of FITC labeled ODN

FITC labeled unmodified and phosphorothioate antisense ODN were kindly provided by Clontech Inc. (Palo Alto, Calif.) FITC was labeled to 3' and 5' of ODN (16 mer). Animal surgery was performed as described above. Transfer of unmodified ODN was performed under two protocols. (1) HVJ complex with FITC labeled unmodified ODN (3 µM) was incubated for 10 minutes. (2) ODN alone: unmodified ODN 30 µM was incubated for 10 minutes. Transfer of phosphorothioate ODN was also performed under two protocols; (1) HVJ complex with FITC labeled phosphorothioate ODN (3 µM) was incubated for 10 minutes. (2) ODN in liposomes without HVJ particles: liposome complex with ODN (3 µM), but without HVJ particles was incubated for 10 minutes. The vessels were harvested at 10 min, 1, 4, 7 and 14 days after transfection and fixed with 3% paraformaldehyde after perfusion of PBS. Sections were examined by fluorescent microscopy, after stained for 5 min in erichrome black T solution and washed twice for 3 min in PBS. Elastic fibers stained dark red and are readily distinguishable from the specific FITC ODN by the treatment by erichrome black T solution.

Reverse transcription (RT)-PCR

RNA was extracted from antisense or sense ODNs (cdk 2 15 µM wrapped in liposomes) treated injured vessels by RNAzol (Tel-Test, Inc., Texas) at 1 and 14 days after transfection. Contralateral arteries were also used in intact arteries. Levels of cdk 2 and beta-actin mRNAs were measured by reverse transcription-PCR. The cdk 2 5' primer (neucleotides −6–12 of human sequences) was 5'-CGCTTCATGGAGAACTTC-3' (SEQ ID NO:46); the 3' primer (neucleotides 340–357) was 5'-ATGGCAGAAAGCTAGGCC-3' (SEQ ID NO:47). The primers complementary to the rat beta-actin gene were 5'-TTGTAACCAACTGGGACGATATGG-3' (SEQ ID NO:48); the 3' primer was 5'-GATCTTGATCTTCATGGTGCTAGG-3' (SEQ ID NO:48) (Clontech Laboratories Inc., Palo Alto, Calif.). Extreme care was taken to avoid contamination of tissue samples with trace amounts of experimental RNA. Aliquots of RNA derived from intact and injured vessels were amplified simultaneously by PCR (35 cycles) and compared with a negative control (primers without RNA). Amplification products were electrophoresed through 2% agarose gels stained with ethidium bromide.

In vivo transfection of antisense ODN

After balloon injury as described above, 500 µl of HVJ-liposomes complex containing sense or antisense cdk 2 or cdc 2 ODN (3 or 15 µM wrapped in liposome) was incubated within lumen for 10 minutes. Direct transfer (cdk 2 ODN; 150 μM) and liposome-mediated transfer without HVJ particle (cdk 2 ODN; 15 μM) were also examined to rat injured carotid arteries. At 2 weeks after transfection, rats were sacrificed and vessels were perfusion-fixed with 4% paraformaldehyde. Neointima formation was assessed by morphometry, by individuals who were blinded to the identity of the samples. Intimal and medial areas were measured on a digitizing tablet (southern Micro Instruments, model 2200, Atlanta, Ga.).

Statistical analysis

All values are expressed as mean±SEM. All experiments were repeated at least three times. Analysis of variance with subsequent Duncan's test was used to determine significant differences in multiple comparisons. P<0.05 was considered significant.

RESULTS

Localization of FITC labeled unmodified and phosphorothioate ODN

Direct transfer of FITC unmodified ODN (30 μM) without HVJ method into rat carotid arteries revealed florescence in the medial layer at 10 minutes after transfection. However, this florescence disappeared 1 day after transfection. In contrast, transfer of FITC unmodified ODN (3 μM) by HVJ method resulted in much wider florescence than direct transfer without HVJ method at 10 min after transfection despite of much lower concentration of ODN. Moreover, the florescence was stimulated in the nuclei and continued up to 1 week after transfection. At 2 weeks after transfection, florescence could not be observed in the medial layer.

A comparison was made of the transfer of FITC labeled phosphorothioate ODN-liposome complex with or without HVJ particles. Florescence in ODN-liposome (3 μM) without HVJ particles transfected vessels was mainly seen in the media layer, but also in the adventitia at 10 min after transfection, similar to direct transfer. This florescence was markedly diminished at 1 day after transfection and disappeared within 4 days. Transfer of FITC labeled phosphorothioate ODN (3 μM) by HVJ method resulted in much wider florescence which was seen at the medial and adventitial layer, and continued up to 2 weeks. This prolongation of florescence was due to the modification of backbone of ODN to phosphorothioate because of their resistance to nuclease. These findings support the utility of phosphorothioate ODN in antisense strategy. At 1 and 2 weeks after transfection, florescence was mainly found in the medial layer, but not in the neointima lesions. The florescence could be observed in the nuclei at this stage. Vessels treated with HVJ complex without ODN revealed no specific immunofluorescence, except autofluorescence in elastic lamina. Florescence resulting from FITC labeled ODN was easily distinguished from autoflorescence. Incubation of free FITC in the vessels did not also result in specific florescence suggesting that this florescence was specific to FITC labeled ODN. Table 6 summarize these results.

TABLE 6

Summary of FITC labeled ODN transfection

| time-course | direct | HVJ-unmodified | liposome | HVJ-S |
|---|---|---|---|---|
| 10 min | + | + | + | + |
| 1 days | nd | + | ± | + |
| 4 days | nd | + | nd | + |
| 7 days |  | + |  | + |
| 14 days |  | nd |  | + | nd = not detected,
± = few florescence,
+ = florescence
direct = direct transfer (30 μM),
HVJ-unmodified = unmodified ODN by HVJ method (3 μM),
liposome = liposome mediated transfer of phosphorothoiate ODN (3 μM) without HVJ particle,
HVJ-S = phosphorothioate ODN (3 μM) by HVJ method.

Reverse-transcriptase PCR of cdk 2 kinase mRNA expression in vivo mRNA expression of cdk 2 in rat carotid injury model was examined to evaluate the specificity of antisense cdk 2 ODN. RNA from the vessels transfected with either antisense or sense cdk 2 ODN (15 μM) was amplified by RT-PCR. At 1 day after injury, RT-PCR of RNA from injured vessels transfected with sense ODN demonstrated a single band corresponding to cdk 2 mRNA, whereas from intact vessels did not. However, administration of cdk 2 ODN abolished the increased mRNA. At least 14 days after injury, RT-PCR of RNA from vessels transfected neither sense nor antisense ODN demonstrated the detectable level of cdk 2 mRNA. In contrast, mRNA of beta-actin was readily detected in the same protocol.

Effect on antisense cdk 2 and cdc 2 ODN

Antisense cdk 2 phosphorothioate ODN was applied to rat injured vessels because the phosphorothioate ODN was found to be stable for 2 weeks in the medial layer by HVJ transfer method. Untreated and sense ODN (2 and 15 μM) transfected vessels exhibited neointimal formation at 2 weeks after transfection. In contrast, a single administration of antisense cdk 2 ODN (3 μM) resulted in a significant reduction in neointima formation (approximately 60% as to compared to sense ODN treated vessels). At high dose of 15 μM, antisense cdk 2 ODN resulted in a further inhibition of neointima formation, but not significantly different. This treatment did not alter the medial areas, suggesting that media viability was not affected by HVJ transfer method. Neointima formation was limited in transfected lesions, but not in untransfected lesions in the same animals (neointimal/medial areas ratio; transfected region=0.597±0.131 vs. untransfected region=1.156±0.079, P<0.01). To investigate the contribution of HVJ transfer to the enhanced lives of ODN in vivo, a comparison was made of the biological action of antisense cdk 2 ODN among the direct transfer, liposome mediated transfer without HVJ particle, and the HVJ method. Both direct transfer (150 μM) and liposome mediated transfer without HVJ particle (15 μM) failed to show any inhibitory effect of antisense ODN.

(1) antisense cdc 2 ODN alone (15 μM), and (2) combination of cdc 2 and cdk 2 ODN (15 μM each) were administered investigate the antisense strategy blocking cell cycle regulatory genes. Administration of antisense cdc 2 ODN partially inhibited neointima formation as well as cdk 2 ODN alone, whereas sense cdc 2 kinase ODN did not. The combination of cdc 2 and cdk 2 ODN showed enhanced inhibition of neointima formation as compared to antisense cdc 2 or cdk 2 ODN alone.

This example demonstrates that HVJ method prolonged the existence of florescence in the medial layer up to 1 week (unmodified ODN) and 2 weeks (phosphorothioate ODN)

after transfection of FITC-labeled ODN, respectively. These findings indicate that the HVJ method bypasses endocytosis. Moreover, the stimulation of florescence in the nuclei that could be seen only by HVJ method may increase the specificity of antisense ODN.

What is claimed is:

1. A method wherein antisense oligodeoxynucleotides (ODVS) complementary to a mRNA encoding a mammalian cyclin-dependent kinase selected from the group consisting of cdc2 and cdk2 are administered to vascular cells lining a mammalian blood vessel, the endothelium of said blood vessel having been injured by balloon catheter injury, which method comprises the steps of:

(a) preparing a composition of said antisense ODNS encapsulated in HVJ-liposomes comprising phosphatidylserine, phosphatidylcholine, and cholesterol in a 1:4.8:2 weight ratio, wherein said ODNS are from 6 to 30 nucleotides and complementary to the initiation codon region of said mRNA encoding said cyclin dependent kinase;

(b) isolating the injured segment of blood vessel with temporary ligatures and (c) infusing a solution of said ODN-HVJ-liposomes into the lumen of said isolated segment of blood vessel via a cannula shortly after said balloon catheter injury to said blood vessel, wherein proliferation of blood vessel cells in said injured segment of blood vessel is inhibited.

2. A method as in claim 1 wherein said ODNs are complementary to the initiation codon region of a mRNA encoding cdk2 and consist of the sequence shown as SEQ ID NO:24.

3. A method as in claim 1 wherein said ODNs are complementary to the initiation codon region of a mRNA encoding cdc2 and consist of the sequence shown as SEQ ID NO:35.

4. A method as in claim 3 wherein said ODNs are a combination of antisense ODN sequences, a first being complementary to the initiation codon region of a mRNA encoding cdc2 and consisting of the sequence shown as SEQ ID NO:35, and a second being complementary to the initiation codon region of a mRNA encoding cyclin B1 and consisting of the sequence shown as SEQ ID NO:43.

5. A method as in claim 3 wherein said ODNs are a combination of antisense ODN sequences, a first being complementary to the initiation codon region of a mRNA encoding cdc2 and consisting of the sequence shown as SEQ ID NO:35, and a second being complementary to the initiation codon region of a mRNA encoding PCNA and consisting of the sequence shown as SEQ ID NO:39.

6. A method as in claim 3 wherein said ODNs are a combination of antisense ODN sequences, a first being complementary to the initiation codon region of a mRNA encoding cdc2 and consisting of the sequence shown as SEQ ID NO:35, and a second being complementary to the initiation codon region of a mRNA encoding cdk2 and consisting of the sequence shown as SEQ ID NO:41.

7. A method according to claim 1 wherein said antisense ODNs are complementary to the initiation codon region of a mRNA encoding a mammalian cdc2.

8. A method as in claim 7 wherein said ODNs are a combination of antisense ODN sequences, a first being complementary to the initiation codon region of a mRNA encoding a mammalian cdc2, and a second being complementary to the initiation codon region of a mRNA encoding a mammalian cdk2.

9. A method as in claim 7 wherein said ODNs are a combination of antisense ODN sequences, a first being complementary to the initiation codon region of a mRNA encoding a mammalian cdc2, and a second being complementary to the initiation codon region of a mRNA encoding a mammalian PCNA.

10. A method as in claim 7 wherein said ODNs are a combination of antisense ODN sequences, a first being complementary to the initiation codon region of a mRNA encoding a mammalian cdc2, and a second being complementary to the initiation codon region of a mRNA encoding a mammalian cyclin B1.

* * * * *